(12) United States Patent
Yang et al.

(10) Patent No.: US 8,119,628 B2
(45) Date of Patent: Feb. 21, 2012

(54) PYRROLIDINE FUSED INDOLOBENZADIAZEPINE HCV NS5B INHIBITORS

(75) Inventors: Zhong Yang, Southington, CT (US); John A. Bender, Middletown, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/922,752

(22) PCT Filed: Mar. 25, 2009

(86) PCT No.: PCT/US2009/038167
§ 371 (c)(1), (2), (4) Date: Oct. 5, 2010

(87) PCT Pub. No.: WO2009/120733
PCT Pub. Date: Oct. 1, 2009

(65) Prior Publication Data
US 2011/0020276 A1    Jan. 27, 2011

Related U.S. Application Data

(60) Provisional application No. 61/039,973, filed on Mar. 27, 2008.

(51) Int. Cl.
| A61P 31/12 | (2006.01) |
| A61K 31/55 | (2006.01) |
| C07D 487/14 | (2006.01) |

(52) U.S. Cl. .................................. 514/214.02; 540/579
(58) Field of Classification Search ............. 514/214.02; 540/579
See application file for complete search history.

(56) References Cited

U.S. PATENT DOCUMENTS

| 7,153,848 | B2 | 12/2006 | Hudyma et al. |
| 7,348,425 | B2 | 3/2008 | Hudyma et al. |
| 7,399,758 | B2 | 7/2008 | Meanwell et al. |
| 7,452,876 | B2 | 11/2008 | Yeung et al. |
| 7,456,165 | B2 | 11/2008 | Bergstrom et al. |
| 7,456,166 | B2 | 11/2008 | Bender et al. |
| 7,456,167 | B2 | 11/2008 | Bergstrom |
| 7,473,688 | B2 | 1/2009 | Bergstrom et al. |
| 7,485,633 | B2 | 2/2009 | Meanwell et al. |
| 7,517,872 | B2 | 4/2009 | Nickel et al. |
| 7,521,441 | B2 | 4/2009 | Gentles et al. |
| 7,521,442 | B2 | 4/2009 | Gentles et al. |
| 7,521,443 | B2 | 4/2009 | Bender et al. |
| 7,521,444 | B2 | 4/2009 | Bender et al. |
| 7,538,102 | B2 | 5/2009 | Yeung et al. |
| 7,538,103 | B2 | 5/2009 | Hewawasam et al. |
| 7,541,351 | B2 | 6/2009 | Bender et al. |
| 7,541,353 | B2 | 6/2009 | Gentles et al. |
| 7,547,690 | B2 | 6/2009 | Gentles et al. |
| 2008/0221090 | A1 | 9/2008 | Yeung et al. |
| 2009/0018163 | A1 | 1/2009 | Schmitz et al. |
| 2009/0130057 | A1 | 5/2009 | Hewawasam et al. |
| 2010/0216774 | A1 | 8/2010 | Bender et al. |

FOREIGN PATENT DOCUMENTS

| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/033032 | 3/2007 |
| WO | WO 2007/092888 | 8/2007 |
| WO | WO 2007/129119 | 11/2007 |
| WO | WO 2009/067108 | 5/2009 |
| WO | WO 2009/067392 | 5/2009 |
| WO | WO 2009/120745 | 10/2009 |

*Primary Examiner* — Brenda Coleman
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and are useful in treating those infected with HCV.

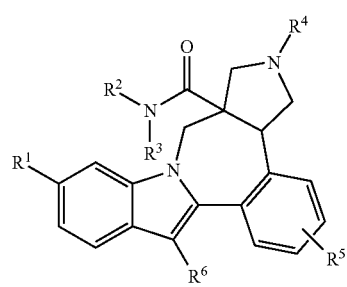

I

12 Claims, No Drawings

PYRROLIDINE FUSED INDOLOBENZADIAZEPINE HCV NS5B INHIBITORS

CROSS-REFERENCE TO RELATED APPLICATIONS

This application claims the benefit of U.S. provisional application Ser. No. 61/039,973 filed Mar. 27, 2008.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

HCV NS5B inhibitors have been disclosed in U.S. Pat. No. 7,399,758.

DESCRIPTION OF THE INVENTION

The invention encompasses compounds of formula I, including pharmaceutically acceptable salts, and compositions and methods of treatment using these compounds.

One aspect of the invention is a compound of formula I

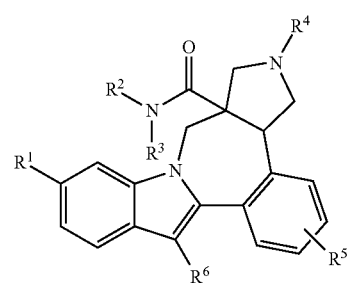

$R^1$ is $CO_2R^7$ or $CONR^8R^9$;

$R^2$ is hydrogen or alkyl;

$R^3$ is hydrogen or alkyl;

or $NR^2R^3$ taken together is azetidinyl, pyrrolidinyl, piperidinyl, piperazinyl, N-(alkyl)piperazinyl, morpholinyl, thiomorpholinyl, homopiperidinyl, or homomorpholinyl, and is substituted with 0-3 alkyl substituents;

or $NR^2R^3$ taken together is

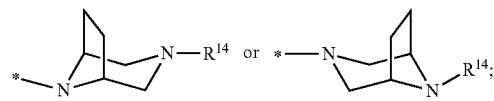

R⁴ is hydrogen, alkyl, alkylCO, (R¹³)alkyl, ((R¹³)alkyl)CO, (R¹³)CO, (R¹³)COCO, (Ar¹)alkyl, (Ar¹)CO, or (Ar¹)COCO;

R⁵ is hydrogen, halo, alkyl, alkenyl, hydroxy, benzyloxy, or alkoxy;

R⁶ is cycloalkyl;

R⁷ is hydrogen or alkyl;

R⁸ is hydrogen, alkyl, alkylSO₂, cycloalkylSO₂, haloalkylSO₂, (R¹⁰)(R¹¹)NSO₂, or (R¹²)SO₂;

R⁹ is hydrogen or alkyl;

R¹⁰ is hydrogen or alkyl;

R¹¹ is hydrogen or alkyl;

R¹² is azetidinyl, pyrrolidinyl, piperidinyl, piperazinyl, N-(alkyl)piperazinyl, morpholinyl, thiomorpholinyl, homopiperidinyl, or homomorpholinyl;

R¹³ is amino, alkylamino, or dialkylamino, or R¹³ is azetidinyl, pyrrolidinyl, piperidinyl, piperazinyl, N-(alkyl)piperazinyl, morpholinyl, thiomorpholinyl, homopiperidinyl, or homomorpholinyl, and is substituted with 0-3 alkyl substituents;

R¹⁴ is hydrogen, alkyl, cycloalkyl, (cycloalkyl)alkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, benzyl, benzyloxycarbonyl, or pyridinyl; and Ar¹ is phenyl, pyrrolyl, pyrazolyl, imidazolyl, or triazolyl, and is substituted with 0-2 alkyl substituents;

or a pharmaceutically acceptable salt thereof.

Another aspect of the invention is a compound of formula I where R¹ is CONR⁸R⁹; R² is alkyl; R³ is alkyl; or NR²R³ taken together is morpholinyl substituted with 2 alkyl substituents; R⁴ is hydrogen, alkyl, alkylCO, (R¹³)alkyl, ((R¹³)alkyl)CO, (R¹³)CO, (R¹³)COCO, (Ar¹)alkyl, or (Ar¹)CO, R⁵ is alkoxy; R⁶ is cycloalkyl; R⁸ is (R¹⁰)(R¹¹)NSO₂; R⁹ is hydrogen; R¹⁰ is alkyl; R¹¹ is alkyl; R¹³ is dialkylamino, or R¹³ is pyrrolidinyl and is substituted with 0-3 alkyl substituents; and Ar¹ is phenyl, or imidazolyl, and is substituted with 0-2 alkyl substituents; or a pharmaceutically acceptable salt thereof.

Another aspect of the invention is a compound of formula I where R¹ is CONHSO₂NMe₂; R² is methyl; R³ is methyl; or NR²R³ taken together is morpholinyl substituted with 2 methyl substituents; R⁴ is hydrogen, methyl, isopropyl, benzyl, acetyl, CONMe₂, N,N-dimethylaminopropyl, COCH₂NMe₂, COCONMe₂, (methylimidazolyl)methyl, (methylimidazolyl)CO, or (methylpyrrolidinyl)CO; R⁵ is methoxy; R⁶ is cyclohexyl; or a pharmaceutically acceptable salt thereof.

Another aspect of the invention is a compound of formula I where R¹ is CONR⁸R⁹; R⁸ is alkylSO₂, cycloalkylSO₂, haloalkylSO₂, (R¹⁰)(R¹¹)NSO₂, or (R¹²)SO₂; and R⁹ is hydrogen.

Another aspect of the invention is a compound of formula I where R⁵ is hydrogen.

Another aspect of the invention is a compound of formula I where R⁵ is methoxy.

Another aspect of the invention is a compound of formula I where R⁶ is cyclohexyl.

Another aspect of the invention is a compound of formula I where R⁸ is (R¹⁰)(R¹¹)NSO₂ or (R¹²)SO₂.

Another aspect of the invention is a compound of formula I with the following stereochemistry.

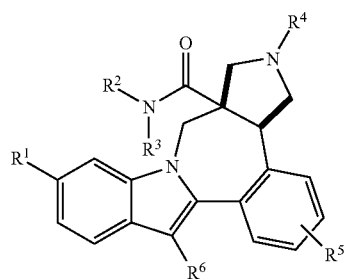

Another aspect of the invention is a compound of formula I with the following stereochemistry.

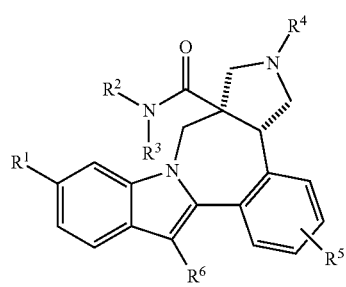

For a compound of Formula I, the scope of any instance of a variable substituent, including R¹, R², R³, R⁴, R⁵, R⁶, R⁷, R⁸, R⁹, R¹⁰, R¹¹, R¹², R¹³, R¹⁴, and Ar¹, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons, "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compounds below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art.

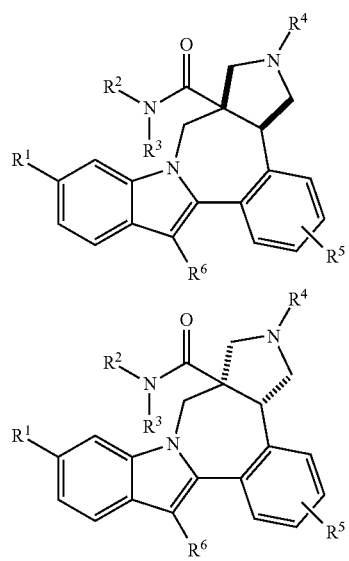

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Alkyl 2-bromo-3-cyclohexyl-1H-indole-6-carboxylates can be hydrolyzed to the corresponding carboxylic acids and coupled to sulfonamides or sulfamides using standard coupling reagents such as carbonyl diimidazole (CDI) or 1-(3-dimethylaminopropyl)-3-ethylcarbodiimide hydrochloride (EDC) (See Scheme 1). The resulting acylsulfonamide/acylsufamide bromoindoles can be subjected to known palladium catalyzed coupling reactions with the substituted or unsubstituted, 2-boronic acid or 2-boronic ester benzaldehydes. The resulting cyclic hemiaminals are sometimes observed to exist in equilibrium with the related aryl aldehydes and can be subjected to a known cyclization utilizing alkyl 2-(dialkoxyphosphoryl)acrylates under basic reaction conditions at elevated temperatures to form substituted 7H-indolo[2,1-a][2]benzazepines.

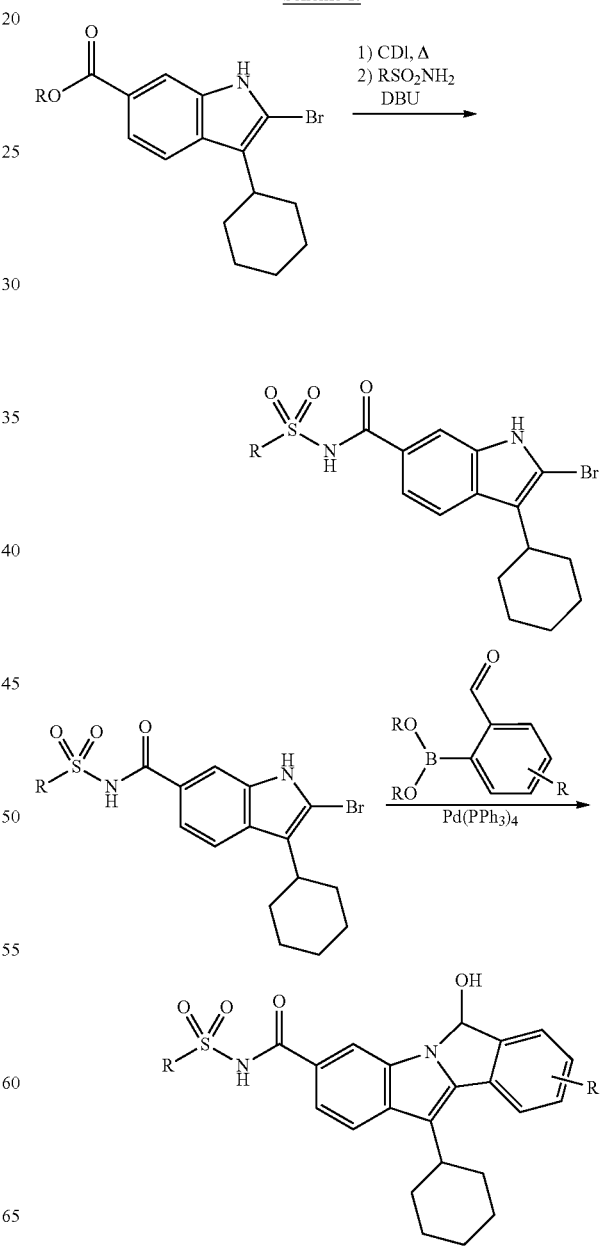

Scheme 1.

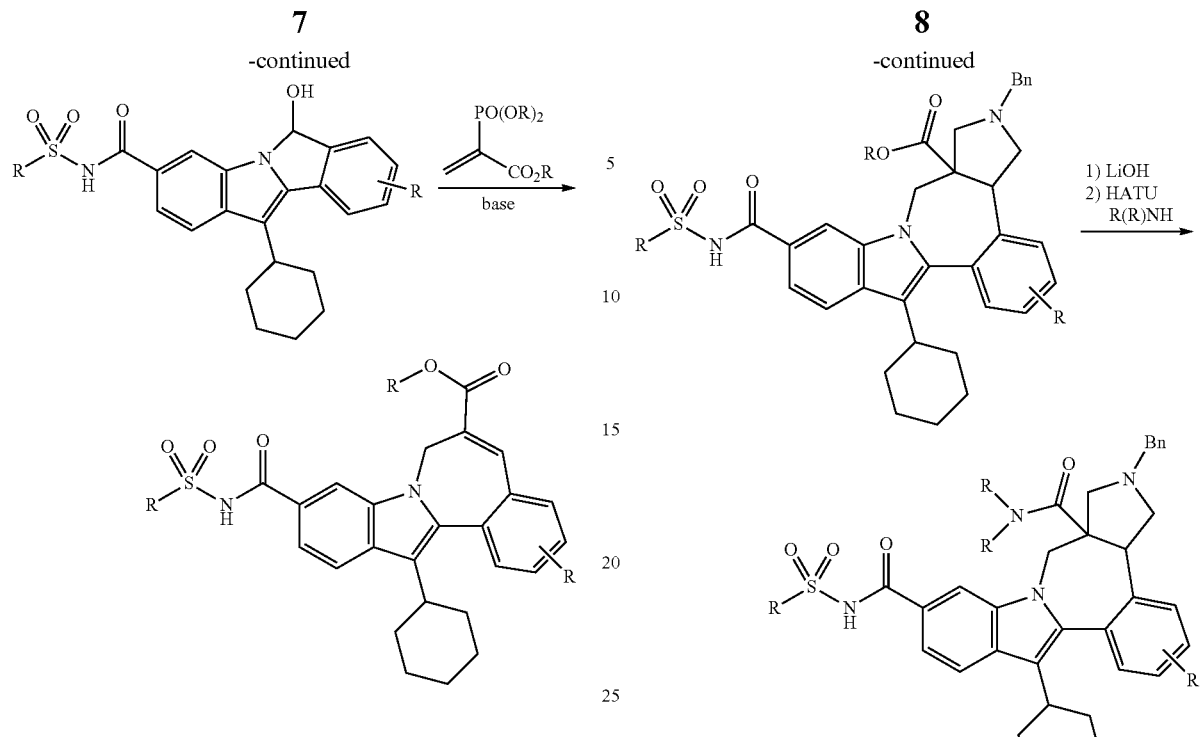

The α,β-unsaturated esters of the 7H-indolo[2,1-a][2]benzazepines can then be reacted with protected N-(alkoxyoxymethyl)-N-(thmethylsilylmethyl)amines to form protected pyrrolidines as formal [3+2]-cycloaddition products (See scheme 2). The neopentyl carboxylic ester can be hydrolyzed and the resulting carboxylic acid can be coupled to a variety of primary or secondary amines using standard amide forming reagents, for example, HATU, CDT, DCC and TBTU. If the pyrrolidine protecting group is a benzyl, hydrogenation can provide useful intermediates in the preparation of molecules presented in this invention.

Scheme 2.

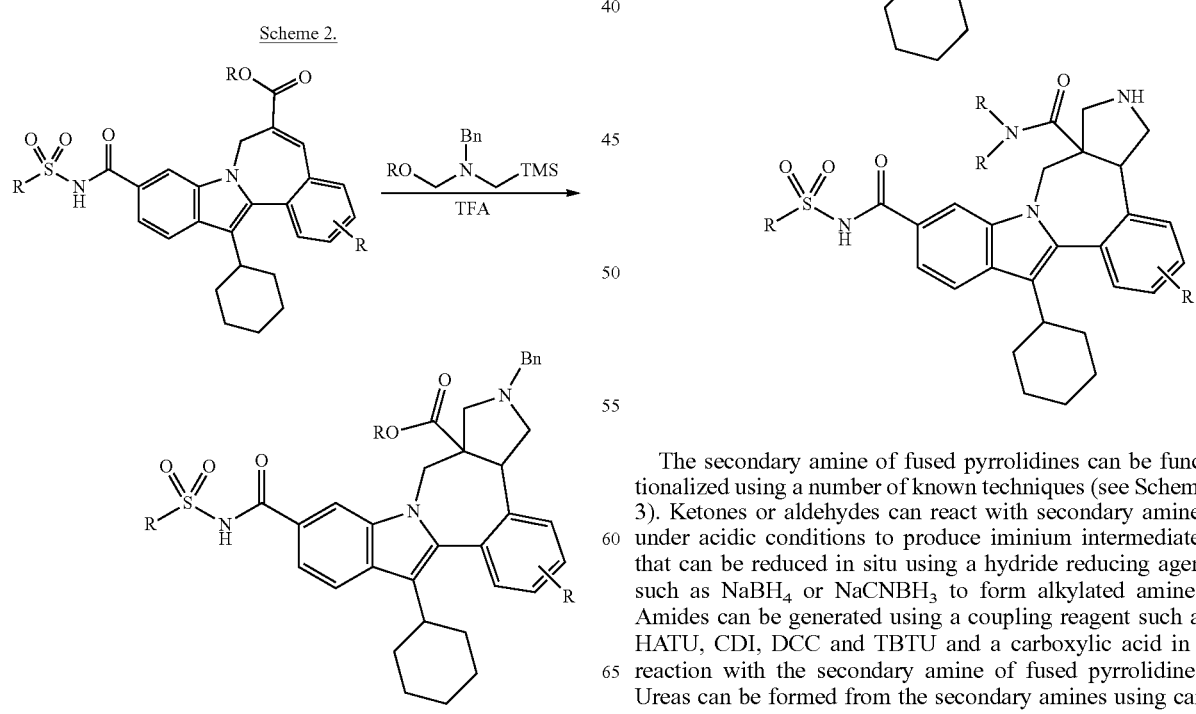

The secondary amine of fused pyrrolidines can be functionalized using a number of known techniques (see Scheme 3). Ketones or aldehydes can react with secondary amines under acidic conditions to produce iminium intermediates that can be reduced in situ using a hydride reducing agent such as $NaBH_4$ or $NaCNBH_3$ to form alkylated amines. Amides can be generated using a coupling reagent such as HATU, CDI, DCC and TBTU and a carboxylic acid in a reaction with the secondary amine of fused pyrrolidines. Ureas can be formed from the secondary amines using carbamyl chlorides under basic reaction conditions.

Scheme 3.

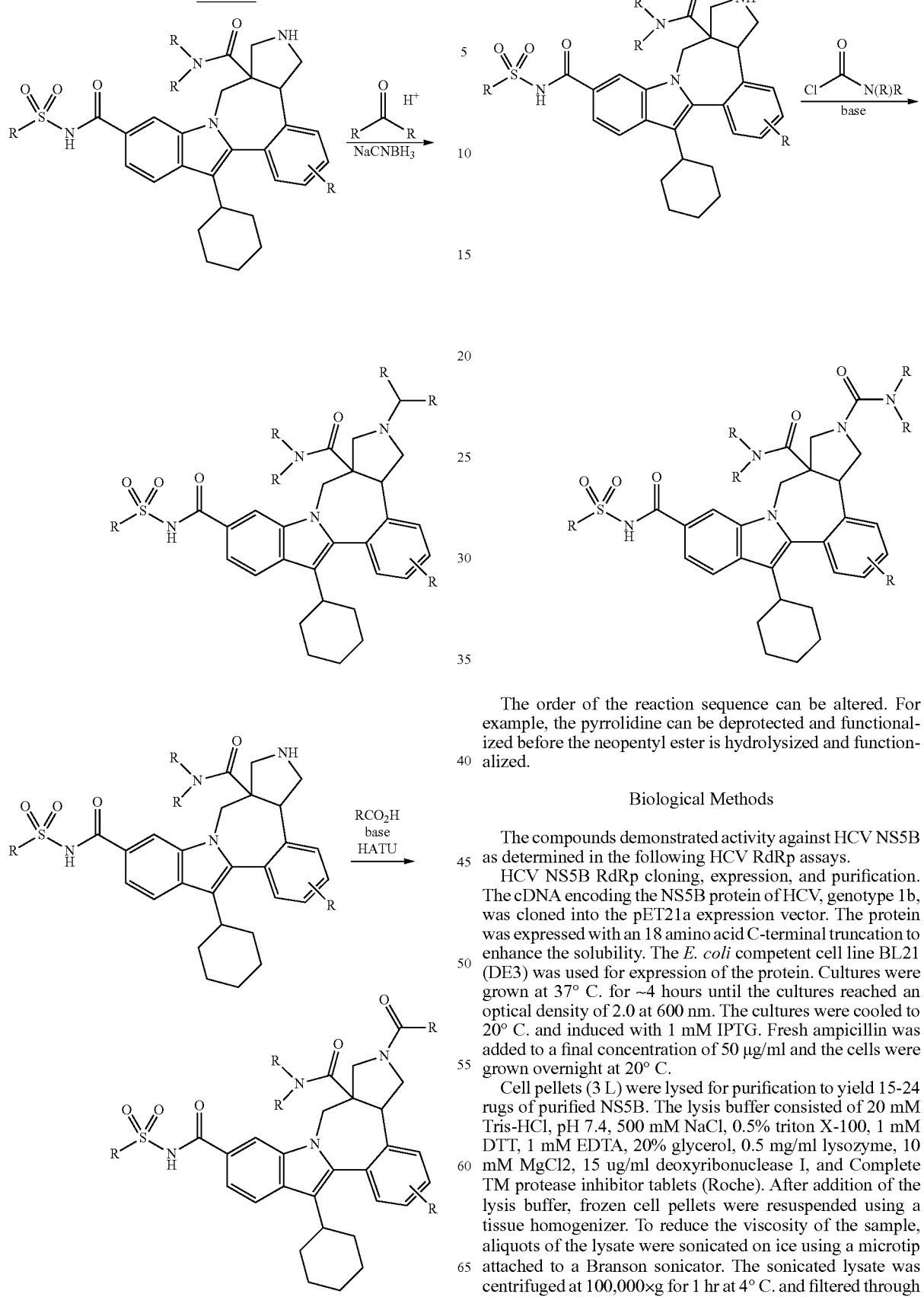

The order of the reaction sequence can be altered. For example, the pyrrolidine can be deprotected and functionalized before the neopentyl ester is hydrolysized and functionalized.

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 rugs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM $MgCl_2$, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 mg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [1]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., Anal. Biochem. 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 uM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Example | Structure | IC$_{50}$ (uM) | EC$_{50}$ (uM) |
|---|---|---|---|
| 1 | 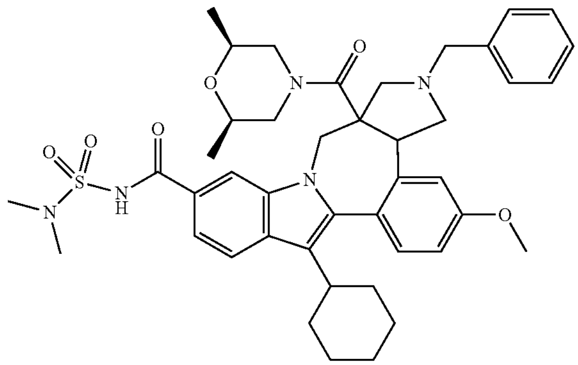 | 0.43 | 0.21 |
| 2 | 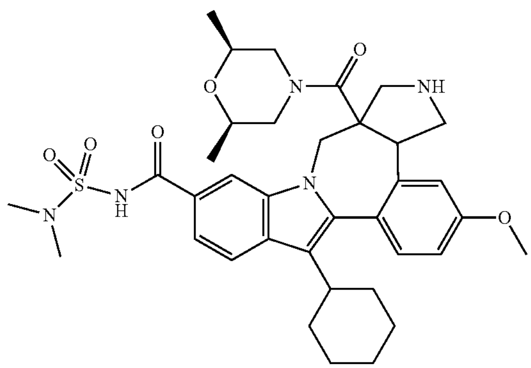 | B | B |
| 3 | 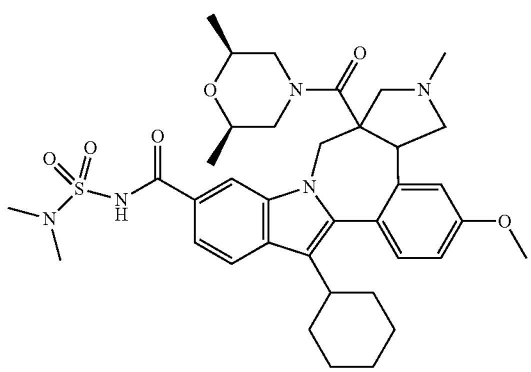 | B | B |
| 4 | 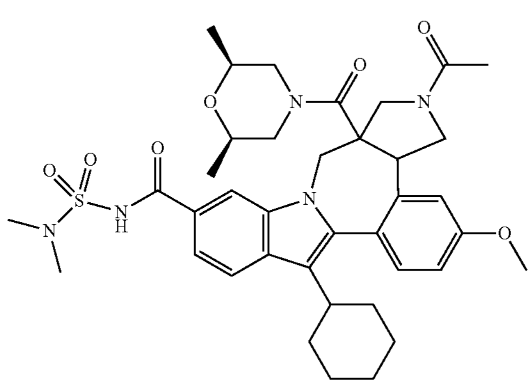 | B | B |

TABLE 1-continued

| Example | Structure | IC$_{50}$ (uM) | EC$_{50}$ (uM) |
|---------|-----------|----------------|----------------|
| 5 | 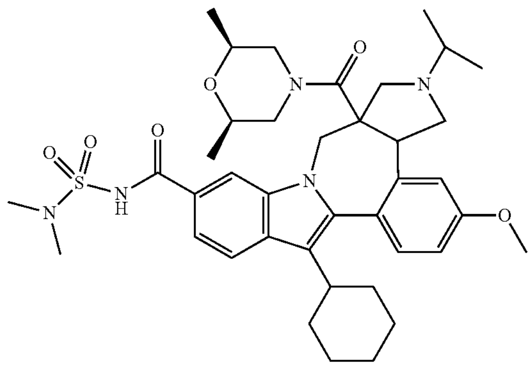 | 0.20 | 0.12 |
| 6 | 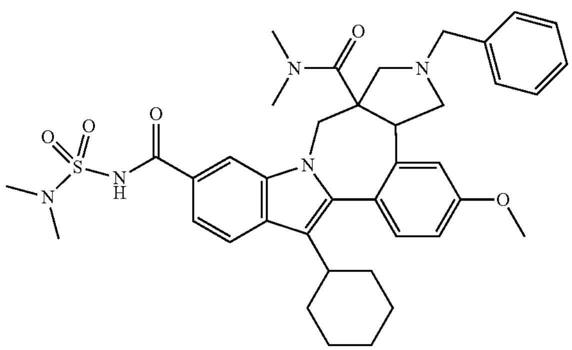 | B | B |
| 7 | 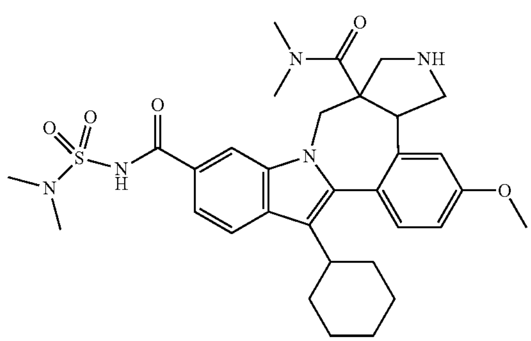 | 0.041 | 0.022 |
| 8 | 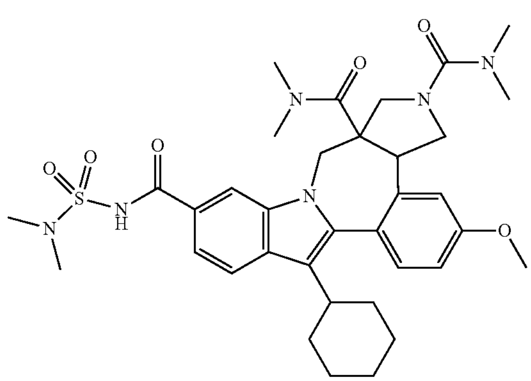 | B | B |

TABLE 1-continued

| Example | Structure | IC$_{50}$ (uM) | EC$_{50}$ (uM) |
|---|---|---|---|
| 9 | 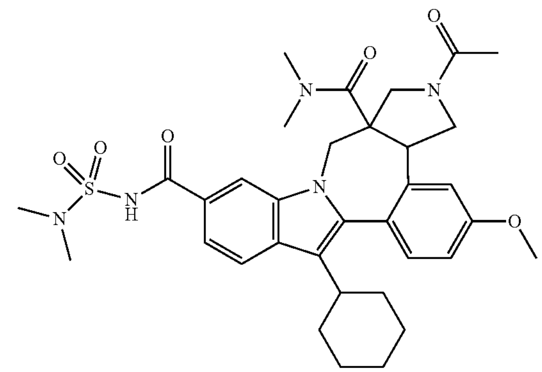 | B | B |
| 10 | 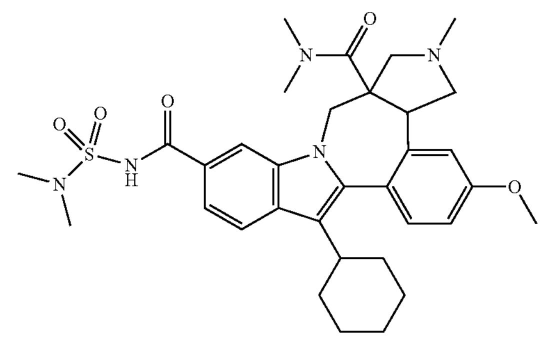 | 0.037 | 0.026 |
| 11 | 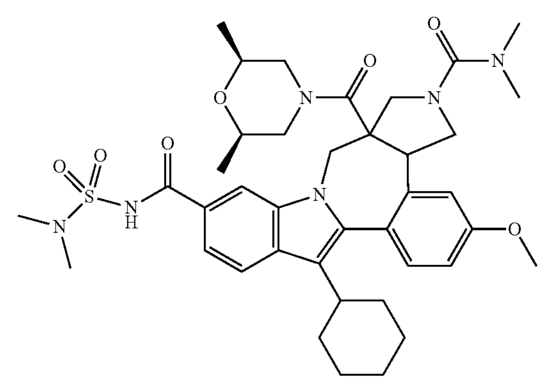 | B | B |
| 12 | 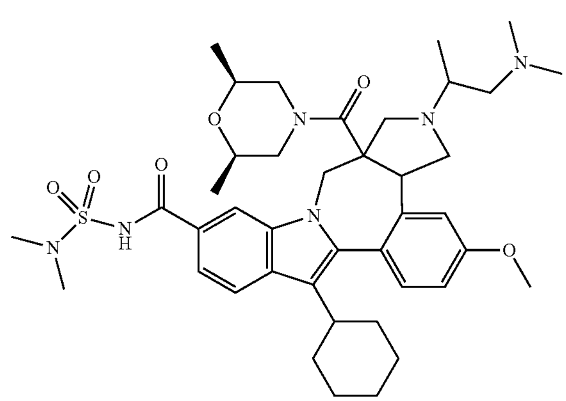 | B | B |

TABLE 1-continued

| Example | Structure | IC$_{50}$ (uM) | EC$_{50}$ (uM) |
|---|---|---|---|
| 13 | 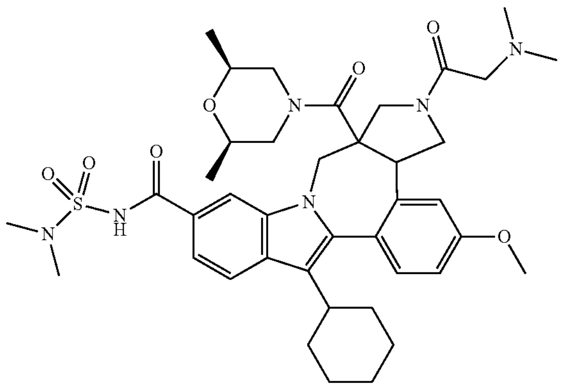 | B | B |
| 14 | 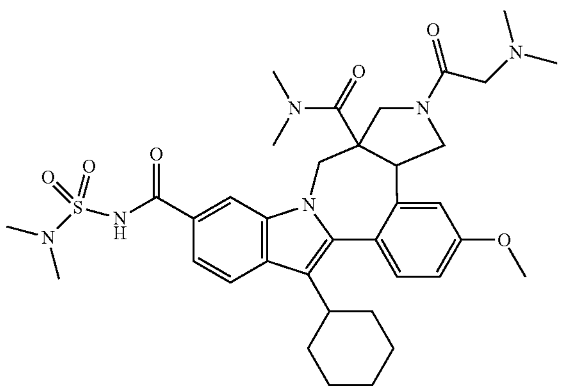 | 0.051 | 0.047 |
| 15 | 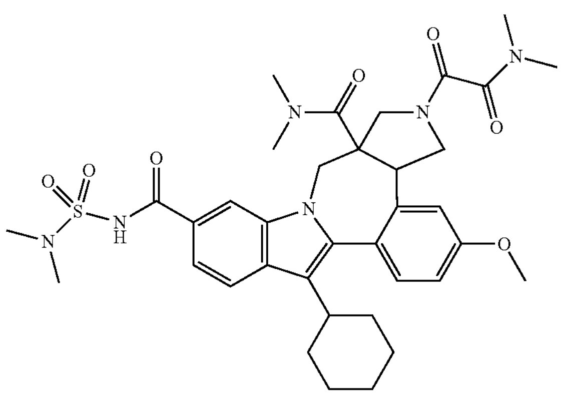 | B | B |
| 16 | 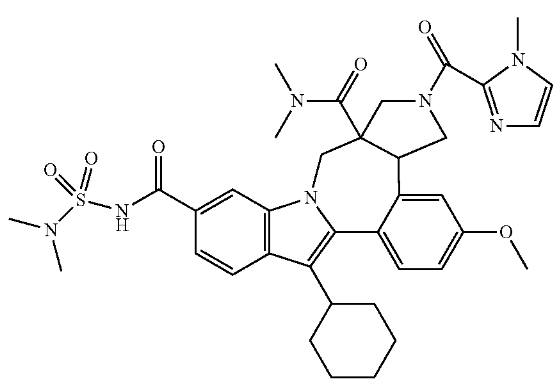 | B | B |

TABLE 1-continued

| Example | Structure | IC$_{50}$ (uM) | EC$_{50}$ (uM) |
| --- | --- | --- | --- |
| 17a | 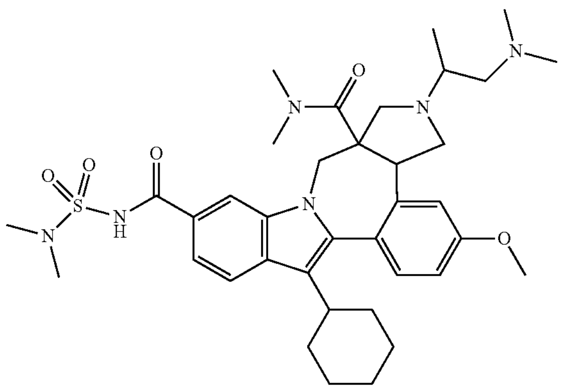 | B | B |
| 17b | 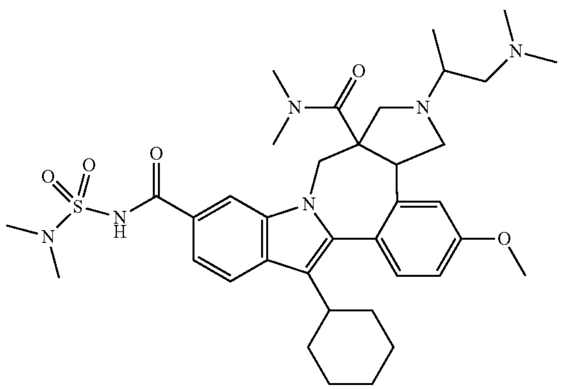 | B | B |
| 18 | 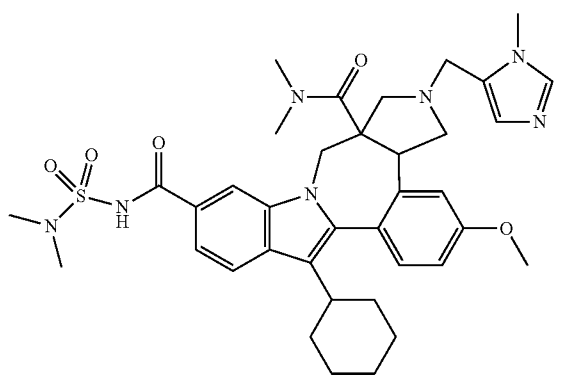 | B | B |
| 19 | 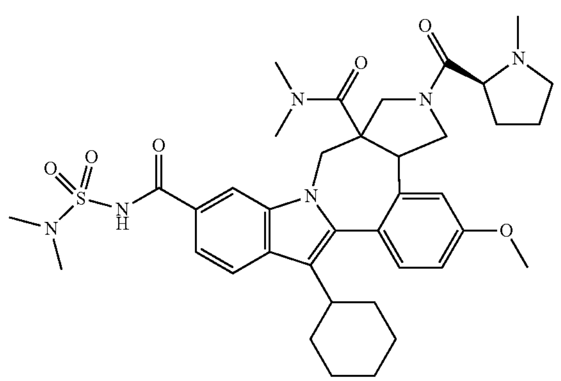 | 0.061 | 0.063 |

A >0.5 μM; B 0.02 μM-0.5 μM; C <0.02 μM but an exact value was not determined; IC$_{50}$ values were determined using the preincubation protocol. EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of hepatitis C.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imigimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, and an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imigimod, ribavirin, an inosine 5-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles.

Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Pharmaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |

TABLE 2-continued

| Brand Name | Type of Inhibitor or Target | Source Company |
|---|---|---|
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Unless otherwise specified, analytical LCMS data on the following intermediates and examples were acquired using the following columns and conditions. Stop time: Gradient time+1 minute; Gradient time: 2 minutes (unless otherwise noted). Starting conc: 0% B unless otherwise noted; Ending conc: 100% B; Eluent A: 10% MeOH/90% $H_2O$ with 0.1% TFA; Eluent B: 90% MeOH/10% $H_2O$ with 0.1% TFA; Column: Phenomenex 10μ 4.6×50 mm C18.

Preparative HPLC data. Gradient: Linear over 20 min. unless otherwise noted; Starting conc: 15% B unless otherwise noted; Ending conc: 100% B; Eluent A: 10% MeOH/90% $H_2O$ with 0.1% TFA; Eluent B: 90% MeOH/10% $H_2O$ with 0.1% TFA; Column: Phenomenex $C_{18}$ 10μ 30×100 mm.

Intermediate 1

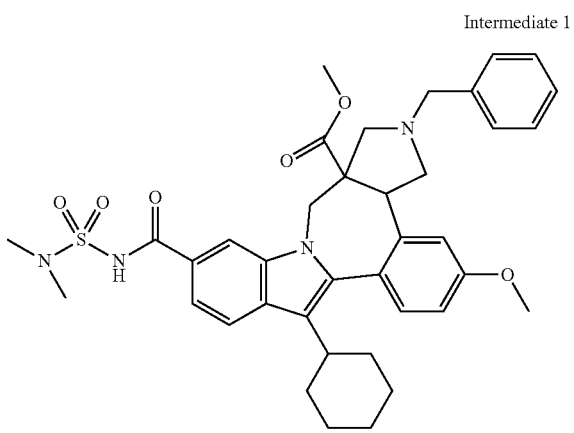

Methyl rac-(3aR,14bR)-2-benzyl-10-cyclohexyl-7-((dimethylsulfamoyl)carbamoyl)-13-methoxy-1,2,3,14b-tetrahydroindolo[2,1-a]pyrrolo[3,4-c][2]benzazepine-3a(4H)-carboxylate. N-(Methoxymethyl)-N-(trimethylsilylmethyl)benzylamine (0.70 mL, 2.7 mmol) was added dropwise to a solution of 13-cyclohexyl-10-((dimethylsulfamoyl)carbamoyl)-3-methoxy-7H-indolo[2,1-a][2]benzazepine-6-carboxylate (500 mg, 0.91 mmol) dissolved into a 5 mM TFA in THF solution (10 mL, 0.050 mmol) under nitrogen. The reaction mixture was stirred 16 h and additional N-(methoxymethyl)-N-(trimethylsilylmethyl)benzylamine (0.40 mL, 1.6 mmol) was added. The reaction mixture was stirred 16 h, quenched with aq NH$_4$Cl (20 mL) and extracted with EtOAc (20 mL). The organic layer was washed with NaHCO$_3$ (20 mL), and brine (15 mL), dried (MgSO$_4$), filtered and concentrated to yield methyl rac-(3aR,14bR)-2-benzyl-10-cyclohexyl-7-((dimethylsulfamoyl)carbamoyl)-13-methoxy-1,2,3,14b-tetrahydroindolo[2,1-a]pyrrolo[3,4-d][2]benzazepine-3a(4H)-carboxylate (990 mg, quant.) as a yellow solid. $^1$H NMR (300 MHz, CD$_3$OD) δ 1.22-1.64 (m, 4H), 1.76-2.36 (m, 7H), 2.87-3.05 (m, 2H), 3.07 (s, 6H), 3.47-3.56 (m, 1H), 3.88 (s, 3H), 3.92 (s, 3H), 3.99-4.16 (m, 4H), 4.32 (d, J=12.8 Hz, 1H), 4.55 (d, J=15.0 Hz, 1H), 6.89-7.29 (m, 5H), 7.10 (d, J=2.6 Hz, 1H), 7.17 (dd, J=8.4, 2.6 Hz, 1H), 7.44 (d, J=8.4 Hz, 1H), 7.68 (dd, J=8.4, 1.1 Hz, 1H), 7.88 (d, J=8.4 Hz, 1H), 8.00 (d, J=1.1 Hz, 1H). LCMS: m/e 685 (M+H)$^+$, ret time 1.87 min, 2 minute gradient.

Intermediate 1

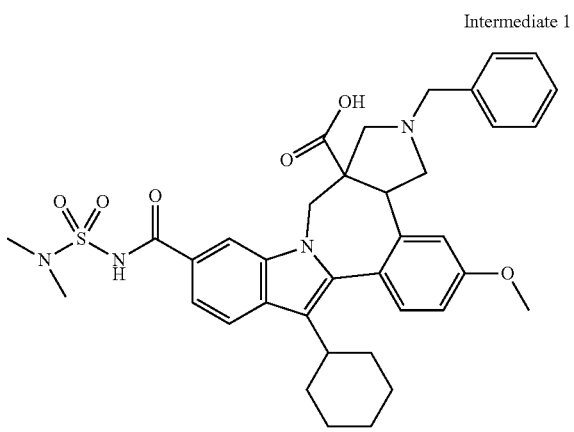

rac-(3aR,14bR)-2-Benzyl-10-cyclohexyl-7-((dimethylsulfamoyl)carbamoyl)-13-methoxy-1,2,3,14b-tetrahydroindolo[2,1-a]pyrrolo[3,4-d][2]benzazepine-3a(4H)-carboxylic acid. A solution of 1.0N aq NaOH (3 mL, 3.0 mmol) was added to a solution of methyl rac-(3aR,14bR)-2-benzyl-10-cyclohexyl-7-((dimethylsulfamoyl)carbamoyl)-13-methoxy-1,2,3,14b-tetrahydroindolo[2,1-a]pyrrolo[3,4-d][2]benzazepine-3a(4H)-carboxylate (620 mg, 0.90 mmol) in THF (10 mL) and MeOH (10 mL). The reaction was stirred for 3d and then concentrated to remove the organic solvents. The residue was diluted with H$_2$O (70 mL), washed with Et$_2$O (2×20 mL), neutralized with 1.0N aq HCl (3 mL, 3.0 mmol) and stirred overnight. The resulting white precipitate was collected by filtration, washed with H$_2$O and dried to yield rac-(3aR,14bR)-2-benzyl-10-cyclohexyl-7-((dimethylsulfamoyl)carbamoyl)-13-methoxy-1,2,3,14b-tetrahydroindolo[2,1-a]pyrrolo[3,4-d][2]benzazepine-3a(4H)-carboxylic acid (596 mg, 0.89 mmol, 99% yield) as a white solid. $^1$H NMR (300 MHz, CD$_3$OD) δ 1.23-1.65 (m, 4H), 1.77-2.39 (m, 7H), 2.87-3.04 (m, 2H), 3.07 (s, 6H), 3.46-3.55 (m, 1H), 3.93 (s, 3H), 3.88-4.18 (m, 4H), 4.32 (d, J=12.4 Hz, 1H), 4.57 (d, J=15.0 Hz, 1H), 6.88-7.30 (m, 6H), 7.18 (dd, J=8.4, 2.6 Hz, 1H), 7.46 (d, J=8.4 Hz, 1H), 7.69 (dd, J=8.8, 1.1 Hz, 1H), 7.89 (d, J=8.8 Hz, 1H), 8.02 (br s, 1H). LCMS: m/e 671 (M+H)$^+$, ret time 3.45 min, 4 minute gradient.

EXAMPLE 1

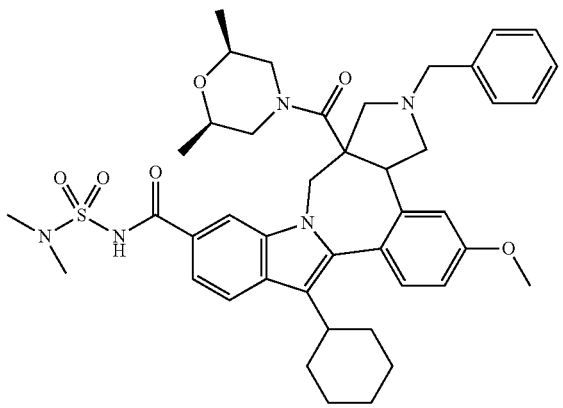

rac-(3aR,14bR)-2-Benzyl-10-cyclohexyl-3a4(2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide. HATU (360 mg, 0.96 mmol) was added to a slurry of rac-(3aR,14bR)-2-benzyl-10-cyclohexyl-7-((dimethylsulfamoyl)carbamoyl)-13-methoxy-1,2,3,14b-tetrahydroindolo[2,1-a]pyrrolo[3,4-d][2]benzazepine-3a(411)-carboxylic acid (490 mg, 0.74 mmol) and (2R,6S)-2,6-dimethylmorpholine (110 mg, 0.96 mmol) in DMF (7 mL) and TEA (0.4 mL, 3.0 mmol). The reaction mixture was stirred at rt for 16 h, diluted with H$_2$O (10 mL) and slowly quenched with aq HCl (1.0N, 3 mL). The resulting off-white precipitate was collected by filtration, washed with H$_2$O and dried to yield the crude product (705 mg) as an off-white solid. A 40 mg portion of the crude product was purified by preparative HPLC (H$_2$O/MeOH with 0.1% TFA buffer) to yield rac-(3aR,14bR)-2-benzyl-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7- carboxamide (26.7 mg, 0.034 mmol, 83%) as an off-white solid ¹H NMR (300 MHz, CD₃OD) δ 1.19 (d, J=6.2 Hz, 3H), 1.21 (d, J=5.9 Hz, 3H), 1.25-1.59 (m, 4H), 1.77-2.33 (m, 8H), 2.82-2.97 (m, 3H), 3.06 (s, 6H), 3.45-3.78 (m, 4H), 3.94 (s, 3H), 3.91-4.12 (m, 4H), 4.27-4.39 (m, 1H), 4.42-4.54 (m, 2H), 6.91-7.30 (m, 5H), 7.18 (dd, J=8.4, 2.6 Hz, 1H), 7.24 (d, J=2.6 Hz, 1H), 7.46 (d, J=8.4 Hz, 1H), 7.69 (dd, J=8.4, 1.1 Hz, 1H), 7.86-7.93 (m, 2H). LCMS: m/e 768 (M+H)⁺, ret time 3.50 min, 4 minute gradient.

EXAMPLE 2

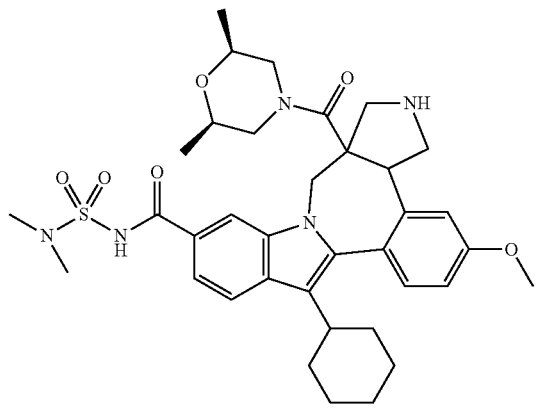

rac-(3aR,14bR)-10-Cyclohexyl-3a4(2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide. 10% Pd/C (60 mg, 0.056 mmol) was added to a cloudy solution of rac-(3aR,14bR)-2-benzyl-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (100 mg, 0.130 mmol) in MeOH/EtOAc/95% EtOH (10:10:1, 21 mL). The reaction mixture was vacuum flushed with N₂ (3×) and then with H₂ (3×) and shaken on a Parr shaker under 50 psi of H₂ for 16 h. The reaction mixture was filtered through celite, and concentrated to a light yellow solid. The crude solid was triturated with MeOH (4 mL+2 mL), to yield rac-(3aR,14bR)-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (40 mg, 0.059 mmol) as a white solid. The mother liquor was concentrated, dissolved into MeOH and DMF, and purified by preparative HPLC (H₂O/MeOH with 0.1% TFA buffer) to yield additional product (27.7 mg, 0.041 mmol) as a light yellow solid. Total isolated product (67.7 mg, 0.10 mmol, 77%). ¹H NMR (300 MHz, CD₃OD) δ 1.23 (d, J=6.2 Hz, 3H), 1.27 (d, J=6.2 Hz, 3H), 1.29-1.70 (m, 4H), 1.77-2.25 (m, 6H), 2.30-2.43 (m, 1H), 2.64-3.05 (m, 3H), 103 (s, 6H), 3.11 (d, J=12.4 Hz, 1H), 3.45 (dd, J=8.1, 11.0 Hz, 1H), 3.59-3.80 (m, 2H), 3.95 (s, 3H), 3.98 (d, J=10.3 Hz, 1H), 4.11 (d, J=15.4 Hz, 1H), 4.10-4.24 (m, 1H), 4.25-4.36 (m, 2H), 4.59 (d, J=15.4 Hz, 1H), 7.19 (dd, J=8.8, 2.6 Hz, 1H), 7.27 (d, J=2.6 Hz, 1H), 7.51 (d, J=8.8 Hz, 1H), 7.67 (dd, J=8.4, 1.5 Hz, 1H), 7.97-8.07 (m, 2H). LCMS: m/e 678 (M+H)⁺, ret time 3.38 min, 4 minute gradient.

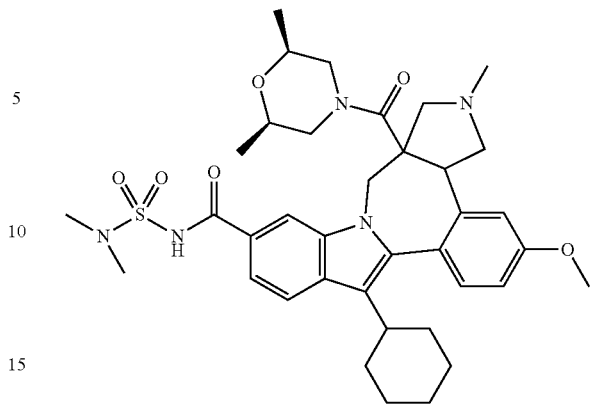

EXAMPLE 3 rac-(3aR,14bR)-10-Cyclohexyl-3a-(((2S,6R)-2,6-dimethyl-4-morpholinyl)carbonyl)-N-(dimethylsulfamoyl)-13-methoxy-2-methyl-1,2,3,3a,4,14b-hexahydroindolo[2,1-a]pyrrolo[3,4-d][2]benzazepine-7-carboxamide. 37% Aqueous formaldehyde (0.03 mL, 0.40 mmol) and then NaCNBH₃ (20 mg, 0.32 mmol) were added to a stirring suspension of rac-(3aR,14bR)-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (30 mg, 0.044 mmol) in MeOH (2 mL). The reaction was stirred overnight at rt, diluted with DMF/MeOH, filtered and purified by preparative HPLC (H₂O/MeOH with 0.1% TFA buffer) to yield rac-(3aR,14bR)-10-cyclohexyl-3a-(((2S,6R)-2,6-dimethyl-4-morpholinyl)carbonyl)-N-(dimethylsulfamoyl)-13-methoxy-2-methyl-1,2,3,3a,4,14b-hexahydroindolo[2,1-a]pyrrolo[3,4-d][2]benzazepine-7-carboxamide (19.6 mg, 0.028 mmol, 64% yield) as an off-white solid. ¹H NMR (500 MHz, CD₃OD) δ 1.21 (d, J=6.1 Hz, 3H), 1.24 (d, J=5.5 Hz, 3H), 1.28-1.38 (m, 1H), 1.42-1.57 (m, 2H), 1.63-1.70 (m, 1H), 1.79-1.90 (m, 2H), 1.95-2.27 (m, 5H), 2.45 (br s, 3H), 2.60-2.93 (m, 3H), 2.95-3.08 (m, 2H), 3.04 (s, 6H), 3.61-3.81 (m, 3H), 3.95 (s, 3H), 4.11-4.45 (m, 3H), 4.53-4.66 (m, 2H), 7.22 (br d, J=8.5 Hz, 1H), 7.26 (br s, 1H), 7.52 (d, J=8.5 Hz, 1H), 7.70 (d, J=8.6 Hz, 1H), 8.01-8.05 (m, 2H). LCMS: m/e 692 (M+H)⁴, ret time 3.40 min, 2 minute gradient.

EXAMPLE 4

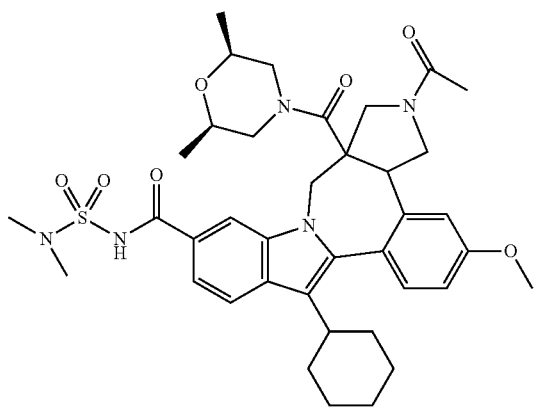

rac-(3aR,14bR)-2-Acetyl-10-cyclohexyl-3a-(((2S,6R)-2, 6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide. HATU (25 mg, 0.066 mmol) was added to a solution of rac-(3aR,14bR)-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (30 mg, 0.044 mmol) and $CH_3CO_2H$ (0.02 mL, 0.35 mmol) in DMF (1 mL) and TEA (0.06 mL, 0.43 mmol). The reaction mixture was stirred at rt for 3 h, diluted with MeOH, and purified by preparative HPLC ($H_2O$/MeOH with 0.1% TFA buffer) to yield product rac-(3aR,14bR)-2-acetyl-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-c]pyrrolo[3,4-d][2]benzazepine-7-carboxamide (16.5 mg, 0.023 mmol, 52% yield) as an off white solid. Complex mixture of rotamers is observed, major rotamer reported. $^1$H NMR (500 MHz, $CD_3OD$) δ 1.11-2.22 (m, 16H), 2.72-3.08 (m, 5H), 3.04 (s, 6H), 3.60-3.80 (m, 3H), 3.92 (s, 3H), 3.86-4.29 (m, 7H), 4.43-4.51 (m, 1H), 4.61 (d, J=15.0 Hz, 1H), 7.08 (dd, J=8.2, 2.5 Hz, 1H), 7.24 (d, J=2.5 Hz, 1H), 7.40 (d, J=8.2 Hz, 1H), 7.61 (d, J=8.6 Hz, 1H), 7.91-7.96 (m, 2H). LCMS: m/e 720 (M+H)$^+$, ret time 3.93 min, 2 minute gradient.

EXAMPLE 5

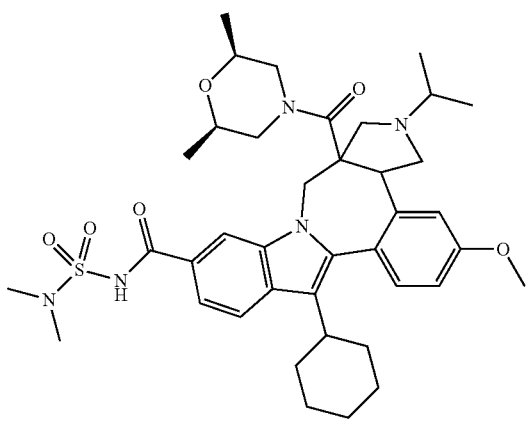

rac-(3aR,14bR)-10-Cyclohexyl-3a-(((2S,6R)-2,6-dimethyl-4-morpholinyl)carbonyl)-N-(dimethylsulfamoyl)-2-isopropyl-13-methoxy-1,2,3,3a,4,14b-hexahydroindolo[2,1-a]pyrrolo[3,4-d][2]benzazepine-7-carboxamide. Acetone (0.050 mL, 0.680 mmol) and then $NaCHBH_3$ (25 mg, 0.40 mmol) were added to a suspension of rac-(3aR,14bR)-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (30 mg, 0.044 mmol) in MeOH (2 mL). The reaction mixture was stirred at rt for 3 h, diluted with DMF/MeOH, and purified by preparative HPLC ($H_2O$/MeOH with 0.1% TFA buffer) to yield a light yellow solid, which was not pure. The impure material was repurified by preparative HPLC ($H_2O$/$CH_3CN$ with 10 mM $NH_4OAc$ buffer) to yield rac-(3aR,14bR)-10-Cyclohexyl-3a-(((2S,6R)-2,6-dimethyl-4-morpholinyl)carbonyl)-N-(dimethylsulfamoyl)-2-isopropyl-13-methoxy-1,2,3,3a,4,14b-hexahydroindolo[2,1-a]pyrrolo[3,4-d][2]benzazepine-7-carboxamide (18.5 mg, 0.026 mmol, 58% yield) as a white solid. $^1$H NMR (300 MHz, $CDCl_3$) 0.50 (d, J=6.6 Hz, 3H), 0.57 (d, J=5.1 Hz, 3H), 1.16-2.14 (m, 16H), 2.37-2.76 (m, 3H), 2.83-3.03 (m, 3H), 3.04 (s, 6H), 3.33 (d, J=10.6 Hz, 1H), 3.53-3.70 (m, 4H), 3.85 (s, 3H), 4.16 (d, J=15.0 Hz, 1H), 4.28 (d, J=15.0 Hz, 1H), 4.38-4.68 (m, 1H), 5.06-5.47 (m, 1H), 6.83 (br s, 1H), 6.93 (dd, J=8.4, 2.2 Hz, 1H), 7.32 (d, J=8.4 Hz, 1H), 7.39 (dd, J=8.4, 1.1 Hz, 1H), 7.84 (d, J=8.4 Hz, 1H), 7.97 (s, 1H).

LCMS: m/e 720 (M+H)$^+$, ret time 3.43 min, 2 minute gradient.

EXAMPLE 6

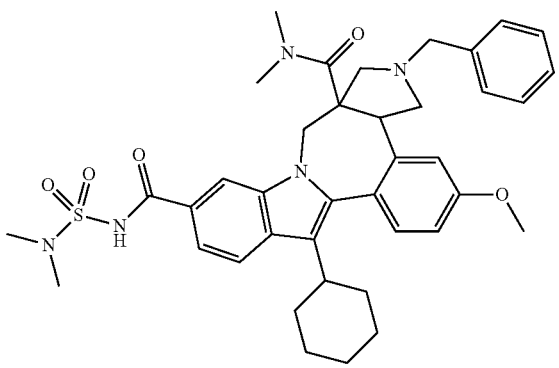

rac-(3aR,14bR)-2-Benzyl-10-cyclohexyl-N$^7$-(dimethylsulfamoyl)-13-methoxy-N$^{3a}$,N$^{3a}$-dimethyl-1,2,3,14b-tetrahydroindolo pyrrolo[3,4-d][2]benzazepine-3a,7(4H)-dicarboxamide. HATU (680 mg, 1.789 mmol) was added to a slurry of rac-(3aR,14bR)-2-benzyl-10-cyclohexyl-7-((dimethylsulfamoyl)carbamoyl)-13-methoxy-1,2,3,14b-tetrahydroindolo[2,1-a]pyrrolo[3,4-d][2]benzazepine-3a(4H)-carboxylic acid (600 mg, 0.89 mmol) and dimethylamine (0.90 mL, 1.8 mmol) in DMF (10 mL) and TEA (0.5 mL, 3.6 mmol). The reaction was stirred overnight, and additional dimethylamine (0.5 mL) and HATU (300 mg) were added. The reaction was stirred overnight, filtered, diluted with $H_2O$ (20 mL) and quenched with 1.0N aq HCl (9 mL) (pH ~3). The organic solvents were removed under reduced pressure and the residue was partitioned between EtOAc (60 mL) and $H_2O$ (40 mL). Organic layer was washed with 1.0N aq HCl (15 mL) and brine (15 mL) and concentrated to a yellow solid. The solid was dissolved into MeOH (30 mL), and $H_2O$ (30 mL) was added dropwise. The resulting precipitate was collected by filtration, washed with 1:1 $H_2O$/MeOH, and dried to yield a crude product (670 mg) as a off white solid. A 15 mg portion of the crude product was purified by preparative HPLC ($H_2O$/MeOH with 0.1% TFA buffer) to yield rac-(3aR,14bR)-2-benzyl-10-cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo[3,4-d][2]benzazepine-3a,7(4H)-dicarboxamide (11.7 mg, 0.017 mmol, 83%) as a white solid. $^1$H NMR (300 MHz, $CD_3OD$) δ 1.24-1.63 (m, 4H), 1.77-2.25 (m, 7H), 2.87-3.04 (m, 2H), 3.07 (s, 6H), 3.10-3.23 (m, 6H), 3.36-3.45 (m, 1H), 3.93 (s, 3H), 3.85-4.09 (m, 3H), 4.39-4.50 (m, 1H), 4.43 (d, J=12.1 Hz, 1H), 4.63 (d, J=15.0 Hz, 1H), 6.91-7.02 (m, 2H), 7.05-7.15 (m, 2H), 7.14 (dd, J=8.4, 2.6 Hz, 1H), 7.20-7.29 (m, 1H), 7.27 (d, J=2.6 Hz, 1H), 7.42 (d, J=8.4 Hz, 1H), 7.70 (dd, J=8.8, 1.5 Hz, 1H), 7.91 (d, J=8.8 Hz, 1H), 7.94 (br s, 1H). LCMS: m/e 698 (M+H)$^+$, ret time 1.90 min, 2 minute gradient.

EXAMPLE 7

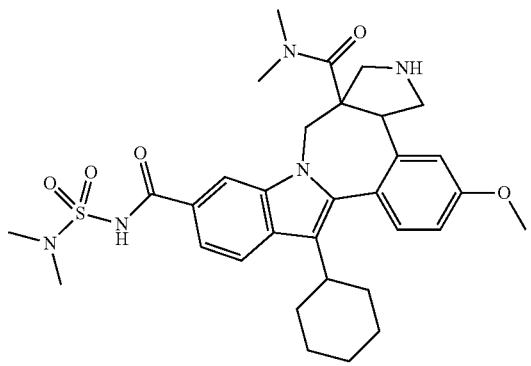

rac-(3aR,14bR)-10-Cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo benzazepine-3a,7(4H)-dicarboxamide. 10% Pd/C (340 mg, 0.32 mmol) was added to a solution of crude rac-(3aR,14bR)-2-benzyl-10-cyclohexyl-N$^7$-(dimethylsulfamoyl)-13-methoxy-N$^{3a}$,N$^{3a}$-dimethyl-1,2,3,14b-tetrahydroindolo[2,1-c]pyrrolo[3,4-d][2]benzazepine-3a,7(4H)-dicarboxamide (535 mg, 0.77 mmol) in MeOH/95% EtOH (10:1, 55 mL). The reaction mixture was vacuum flushed with N$_2$ (3×) and with H$_2$ (3×) and shaken on a Parr shaker under 50 psi of H$_2$ for 16 h. The reaction mixture was filtered through celite, and concentrated to a light yellow solid. The crude solid was triturated with MeOH, to yield rac-(3aR,14bR)-10-cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo[3,4-d][2]benzazepine-3a,7(4H)-dicarboxamide (336 mg, 0.553 mmol, 72% yield) as a white solid. $^1$H NMR (300 MHz, CD$_3$OD) δ 1.24-2.33 (m, 11H), 2.86-3.05 (m, 2H), 3.04 (s, 6H), 3.12-3.25 (m, 6H), 3.95 (s, 3H), 3.93-4.07 (m, 2H), 4.42 (d, J=12.8 Hz, 1H), 4.59 (dd, J=13.9, 7.7 Hz, 1H), 4.74-4.81 (m, 2H), 7.17 (dd, J=8.8, 2.6 Hz, 1H), 7.30 (d, J=2.6 Hz, 1H), 7.48 (d, J=8.8 Hz, 1H), 7.69 (dd, J=8.4, 1.5 Hz, 1H), 8.00 (d, J=8.4 Hz, 1H), 8.14 (d, J=1.5 Hz, 1H). LCMS: m/e 608 (M+H)$^+$, ret time 1.82 min, 2 minute gradient.

EXAMPLE 8

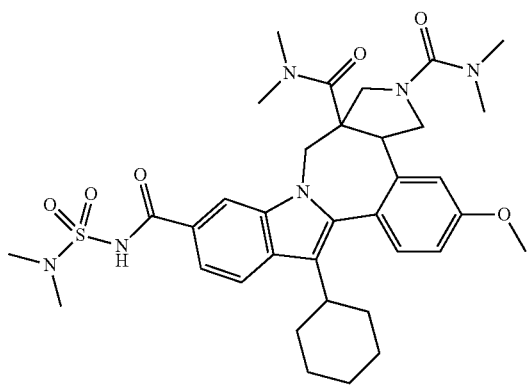

rac-(3aR,14bR)-10-Cyclohexyl-N$^7$-(dimethylsulfamoyl)-13-methoxy-N$^2$,N$^2$,N$^{3a}$,N$^{3a}$-tetramethyl-1,14b-dihydroindolo[2,1-a]pyrrolo[3,4-d][2]benzazepine-2,3a,7 (3H,4H)-tricarboxamide. Dimethylcarbamyl chloride (0.020 mL, 0.22 mmol) and iPr$_2$EtN (0.040 mL, 0.23 mmol) were added to a solution of rac-(3aR,14bR)-10-cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo[3,4-d][2]benzazepine-3a,7(4H)-dicarboxamide (30 mg, 0.049 mmol) in THF (1 mL). The reaction mixture was stirred at rt for 16 h, diluted with MeOH/DMF and purified by preparative HPLC (H$_2$O/CH$_3$CN with 10 mM NH$_4$OAc buffer) to yield rac-(3aR,14bR)-10-cyclohexyl-N$^7$-(dimethylsulfamoyl)-13-methoxy-N$^2$,N$^2$,N$^{3a}$,N$^{3a}$-tetramethyl-1,14b-dihydroindolo[2,1-a]pyrrolo[3,4-d][2]benzazepine-2,3a,7(3H,4H)-tricarboxamide (10.5 mg, 0.015 mmol, 31% yield) as a white solid. $^1$H NMR (300 MHz, CDCl$_3$) δ 1.11-1.55 (m, 4H), 1.68-2.14 (m, 7H), 237 (s, 6H), 2.55-2.65 (m, 1H), 3.04 (s, 6H), 2.85-3.11 (m, 5H), 3.38 (t, J=9.9 Hz, 1H), 3.87 (s, 3H), 3.80-4.02 (m, 3H), 4.18 (d, J=12.1 Hz, 1H), 4.28 (dd, J=10.6, 10.2 Hz, 1H), 4.55 (d, J=15.0 Hz, 1H), 6.95 (dd, J=8.4, 2.2 Hz, 1H), 7.20 (d, J=2.2 Hz, 1H), 7.31 (d, J=8.4 Hz, 1H), 7.43 (d, J=8.4 Hz, 1H), 7.83 (d, J=8.4 Hz, 1H), 8.00 (s, 1H). LCMS: m/e 679 (M+H)$^+$, ret time 3.86 min, 4 minute gradient.

EXAMPLE 9

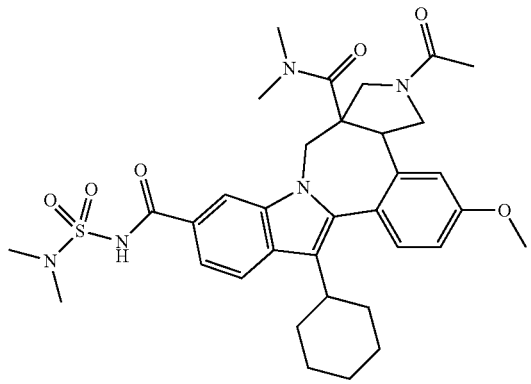

rac-(3aR,14bR)-2-Acetyl-10-cyclohexyl-N$^7$-(dimethylsulfamoyl-13-methoxy-N$^{3a}$,N$^{3a}$-dimethyl-1,2,3,14b-tetrahydroindolo[2,1-a]pyrrolo[3,4-d][2]benzazepine-3a,7 (4H)-dicarboxamide. HATU (38 mg, 0.10 mmol) was added to a solution of rac-(3aR,14bR)-10-cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo[3,4-d][2]benzazepine-3a,7(4H)-dicarboxamide (30 mg, 0.049 mmol) and CH$_3$CO$_2$H (0.020 mL, 0.35 mmol) in DMF (1 mL) and TEA (0.060 mL, 0.43 mmol). The reaction mixture was stirred at rt for 3 h, neutralized by the dropwise addition of 0.2 M aq HCl (1 mL) and concentrated to dryness. The residue was partitioned between EtOAc (5 mL) and H$_2$O (5 mL) and the aqueous layer was extracted with EtOAc (5 mL). The combined organic layers were washed with brine, concentrated and purified by preparative HPLC (H$_2$O/CH$_3$CN with 10 mM NH$_4$OAc buffer) to yield rac-(3aR,14bR)-2-acetyl-10-cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo[3,4-d][2]benzazepine-3a,7(4H)-dicarboxamide (15 mg, 0.023 mmol, 47% yield) as a white solid. Complex mixture of rotamers is observed, partial $^1$H NMR (aromatic region) reported for two major rotamers (~2:1 ratio). $^1$H NMR (300 MHz, CD$_3$OD) δ 7.05-7.11 (m, 1H), 7.23 (d, J=2.6 Hz, 0.3H), 7.27 (d, J=2.6

Hz, 0.7H), 7.40 (d, J=8.8 Hz, 0.3H), 7.41 (d, J=8.8 Hz, 0.7H), 7.63 (dd, J=8.4, 1.5 Hz, 0.3H), 7.65 (dd, J=8.4, 1.5 Hz, 0.7H), 7.91 (d, J=8.4 Hz, 0.3H), 7.93 (d, J=8.4 Hz, 0.7H), 8.10 (br s, 0.7H), 8.13 (br s, 0.3H). LCMS: m/e 650 (M+H)+, ret time 3.76 min, 4 minute gradient.

EXAMPLE 10

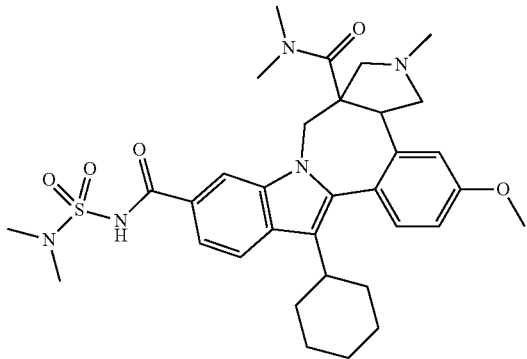

rac-(3aR,14bR)-10-Cyclohexyl-N$^7$-(dimethylsulfamoyl)-13-methoxy-N$^{3a}$,N$^{3a}$,2-trimethyl-1,2,3,14b-tetrahydroindolo[2,1-a]pyrrolo[3,4-d][2]benzazepine-3a,7(4H)-dicarboxamide. 37% Aqueous formaldehyde (0.03 mL, 0.4 mmol) and then NaCNBH$_3$ (20 mg, 0.32 mmol) were added to a stirring suspension of rac-(3aR,14bR)-10-cyclohexyl-N$^7$-(dimethylsulfamoyl)-13-methoxy-N$^{3a}$,N$^{3a}$-dimethyl-1,2,3,14b-tetrahydroindolo[2,1-a]pyrrolo[3,4-d][2]benzazepine-3a,7(4H)-dicarboxamide (30 mg, 0.049 mmol) in MeOH (1.5 mL). The reaction mixture was stirred at rt for 3 h, diluted with DMF/MeOH, and purified by preparative HPLC (H$_2$O/MeOH with 0.1% TFA buffer) to yield rac-(3aR,14bR)-10-cyclohexyl-N$^7$-(dimethylsulfamoyl)-13-methoxy-N$^{3a}$,N$^{3a}$,2-trimethyl-1,2,3,14b-tetrahydroindolo[2,1-a]pyrrolo[3,4-d][2]benzazepine-3a,7(4H)-dicarboxamide (19.4 mg, 0.031 mmol, 63% yield) as a white solid. $^1$H NMR (300 MHz, CDCl$_3$) δ 1.22-2.24 (m, 11H), 2.44 (br s, 3H), 2.94-3.02 (m, 2H), 3.04 (s, 6H), 3.16 (br s, 6H), 3.52-3.67 (m, 1H), 3.94 (s, 3H), 4.09 (d, J=15.4 Hz, 1H), 4.40-4.63 (m, 2H), 4.74 (d, J=15.4 Hz, 1H), 7.18 (dd, J=8.4, 2.6 Hz, 1H), 7.29 (d, J=2.6 Hz, 1H), 7.48 (d, J=8.4 Hz, 1H), 7.71 (dd, J=8.4, 1.5 Hz, 1H), 8.03 (d, J=8.4 Hz, 1H), 8.12 (br 5, 1H). LCMS: m/e 622 (M+H)+, ret time 3.23 min, 4 minute gradient.

EXAMPLE 11

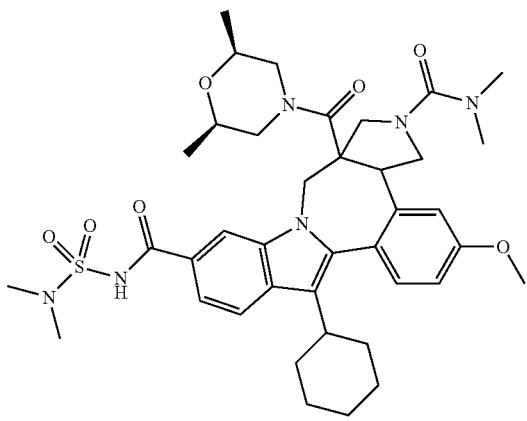

rac-(3aR,14bR)-10-Cyclohexyl-3a4(2S,6R)-2,6-dimethyl-4-morpholinyl)carbonyl)-N$^7$-(dimethylsulfamoyl)-13-methoxy-N$^2$,N$^2$-dimethyl-1,3a,4,14b-tetrahydroindolo[2,1-a]pyrrolo[3,4-d][2]benzazepine-2,7(3H)-dicarboxamide. Dimethylcarbamyl chloride (0.010 mL, 0.11 mmol) and then iPr$_2$EtN (0.031 mL, 0.18 mmol) were added to a suspension of rac-(3aR,14bR)-10-cyclohexyl-3a4(2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (30 mg, 0.044 mmol) in THF (1.5 mL). The reaction mixture was stirred at rt for 16 h, diluted with MeOH/DMF, and purified by preparative HPLC (H$_2$O/MeOH with 0.1% TFA buffer) to yield rac-(3aR,14bR)-10-cyclohexyl-3a-(((2S,6R)-2,6-dimethyl-4-morpholinyl)carbonyl)-N$^7$-(dimethylsulfamoyl)-13-methoxy-N$^2$,N$^2$-dimethyl-1,3a,4,14b-tetrahydroindolo[2,1-c]pyrrolo[3,4-d][2]benzazepine-2,7(3H)-dicarboxamide (17.1 mg, 0.023 mmol, 52% yield) as a white solid. 3:1 Mixture of rotamers. $^1$H NMR (300 MHz, CD$_3$OD) δ 1.24 (d, J=6.2 Hz, 3H), 1.28 (d, J=6.2 Hz, 3H), 1.30-2.27 (m, 10H), 2.49 (s, 4.5H), 2.65-2.84 (m, 2H), 2.86-2.90 (m, 1H), 2.94 (s, 1.5H), 2.99-3.02 (m, 1H), 3.03 (s, 6H), 3.49-3.58 (m, 1H), 3.60-3.85 (m, 3.75H), 3.88 (s, 0.75H), 3.91 (s, 2.25H), 3.95-4.27 (m, 4.25H), 4.56 (d, J=15.0 Hz, 0.75H), 4.73-4.80 (m, 0.25H), 6.84 (br s, 0.25H), 7.03-7.08 (m, 0.25H), 7.07 (dd, J=8.4, 2.6 Hz, 0.75H), 7.17 (d, J=2.6 Hz, 0.75H), 7.34 (d, J=8.4 Hz, 0.25H), 7.41 (d, J=8.4 Hz, 0.75H), 7.55 (br d, J=8.4 Hz, 0.25H), 7.61 (dd, J=8.4, 1.5 Hz, 0.75H), 7.87 (d, J=8.4 Hz, 0.25H), 7.92 (d, J=8.4 Hz, 0.75H), 7.99 (br s, 0.25H), 8.02 (d, J=1.5 Hz, 0.75H). LCMS: m/e 749 (M+H)+, ret time 4.01 min, 4 minute gradient.

EXAMPLE 12

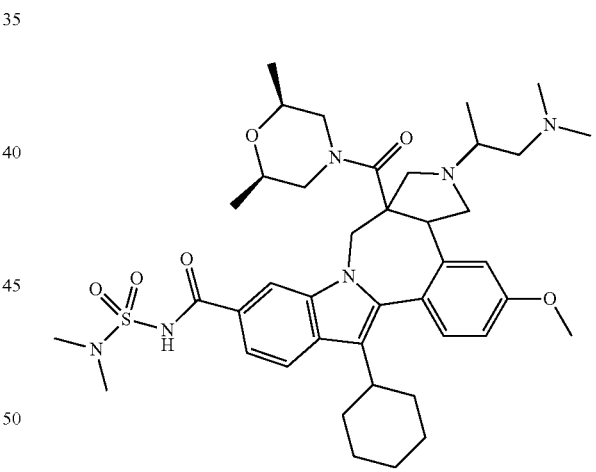

rac-(3aR,14bR)-10-Cyclohexyl-2-(2-(dimethylamino)-1-methylethyl)-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carbaxamide. (Dimethylamino)acetone (0.020 mL, 0.18 mmol) and then NaCNBH$_3$ (11 mg, 0.18 mmol) were added to a suspension of rac-(3aR,14bR)-10-cyclohexyl-3a4(2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (30 mg, 0.044 mmol) in MeOH (2 mL). The reaction mixture was stirred at rt for 16 h, diluted with DMF, and purified by preparative HPLC (H$_2$O/MeOH with 0.1% TFA buffer) to yield a yellow solid which was repurified by preparative HPLC (H₂O/CH₃CN with 10 mM NH₄OAc buffer) to yield rac-(3aR,14bR)-10-cyclohexyl-2-(2-(dimethylamino)-1-methylethyl)-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (118 mg, 0.018 mmol, 41% yield) as a white solid. ¹H NMR (300 MHz, CD₃OD) δ 0.07 (d, J=6.2 Hz, 3H), 1.24 (d, J=6.2 Hz, 3H), 1.32 (d, J=5.5 Hz, 3H), 1.38-2.24 (m, 10H), 2.71 (br, 6H), 2.97 (br, 6H), 2.60-3.07 (m, 8H), 3.56 (d, J=10.3 Hz, 1H), 3.59-3.79 (m, 2H), 3.92 (s, 3H), 3.89-3.98 (m, 1H), 4.15 (dd, J=11.3, 7.7 Hz, 1H), 4.25-4.38 (m, 2H), 4.45 (d, J=14.6 Hz, 1H), 4.73-4.80 (m, 1H), 7.08 (dd, J=8.4, 2.6 Hz, 1H), 7.18 (d, J=2.6 Hz, 1H), 7.41 (d, J=8.4 Hz, 1H), 7.70 (br d, J=8.4 Hz, 1H), 7.89 (d, J=8.4 Hz, 1H), 8.07 (br s, 1H). LCMS: m/e 763 (M+H)⁺, ret time 3.58 min, 4 minute gradient.

EXAMPLE 13

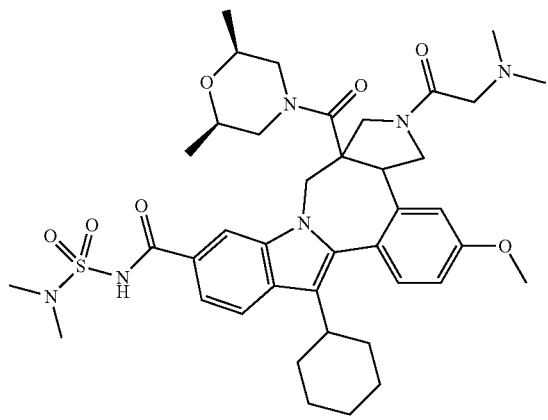

rac-(3aR,14bR)-10-Cyclohexyl-2-(N,N-dimethylglycyl)-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide. N,N-Dimethylglycine (9.1 mg, 0.089 mmol) and then HATU (25.2 mg, 0.066 mmol) were added to a suspension of rac-(3aR,14bR)-10-cyclohexyl-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (30 mg, 0.044 mmol) in DMF (1.5 mL) and TEA (0.031 mL, 0.22 mmol). The reaction mixture was stirred at rt for 16 h, diluted with MeOH, and purified by preparative HPLC (H₂O/MeOH with 0.1% TPA buffer) to yield a solid which was repurified by preparative HPLC (H₂O/CH₃CN with 10 mM NH₄OAc buffer) to yield rac-(3aR,14bR)-10-cyclohexyl-2-(N,N-dimethylglycyl)-3a-(((2S,6R)-2,6-dimethyl-4-morpholinyl)carbonyl)-N-(dimethylsulfamoyl)-13-methoxy-1,2,3,3a,4,14b-hexahydroindolo[2,1-a]pyrrolo[3,4-d][2]benzazepine-7-carboxamide (16.0 mg, 0.021 mmol, 47% yield) as a white solid. 1:1 Mixture of rotamers. ¹H NMR (300 MHz, CD₃OD) δ 1.21-1.38 (m, 6H), 1.38-2.19 (m, 12H), 2.38 (s, 3H), 2.54-3.08 (m, 12H), 3.46-3.81 (m, 4H), 3.93 (s, 3H), 3.88-4.52 (m, 6H), 4.64 (d, J=15.0 Hz, 0.5H), 4.66 (d, J=14.6 Hz, 0.5H), 7.05-7.12 (m, 1H), 7.23 (d, J=2.6 Hz, 0.5H), 7.25 (d, J=2.6 Hz, 0.5H), 7.41 (d, J=8.4 Hz, 0.5H), 7.43 (d, J=8.4 Hz, 0.5H), 7.66 (dd, J=8.4, 1.5 Hz, 0.5H), 7.72 (dd, J=8.4, 1.5 Hz, 0.5H), 7.82 (d, J=8.4 Hz, 0.5H), 7.88 (d, J=8.8 Hz, 0.5H), 8.04 (br s, 0.5H), 8.15 (br s, 0.5H). LCMS: m/e 763 (M+H)⁺, ret time 3.45 min, 4 minute gradient.

EXAMPLE 14

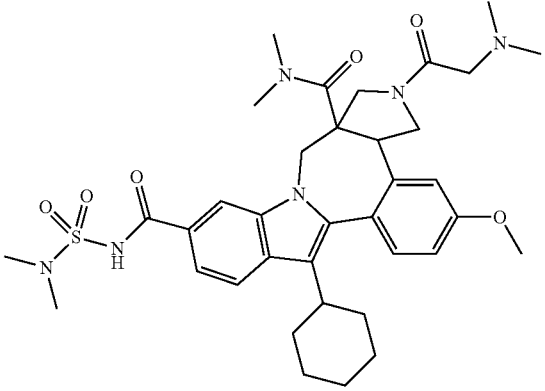

rac-(3aR,14bR)-10-Cyclohexyl-2-(N,N-dimethylglycyl)-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4H)-dicarboxamide. HATU (37.5 mg, 0.099 mmol) was added to a solution of rac-(3aR,14bR)-10-cyclohexyl-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4H)-dicarboxamide (30 mg, 0.049 mmol) and 2-(dimethylamino)acetic acid (10 mg, 0.10 mmol) in DMF (1 mL) and TEA (0.03 mL, 0.215 mmol). The reaction mixture was stirred at rt for 3 h, diluted with MeOH, and purified by preparative HPLC (H₂O/MeOH with 0.1% TPA buffer) to yield rac-(3aR,14bR)-10-cyclohexyl-2-(N,N-dimethylglycyl)-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4H)-dicarboxamide (15.5 mg, 0.022 mmol, 45% yield) as a white solid. 1:1 Mixture of rotamers. ¹H NMR (300 MHz, CD₃OD) δ 1.22-2.23 (m, 10H), 2.34-3.09 (m, 9H), 3.04 (s, 3H), 3.05 (s, 3H), 3.12-3.28 (m, 4H), 3.42-3.71 (m, 2H), 3.94 (s, 3H), 3.83-4.13 (m, 4H), 4.31-4.58 (m, 2H), 4.82-4.96 (m, 1H), 7.08-7.14 (m, 1H), 7.27 (d, J=2.6 Hz, 0.5H), 7.29 (d, J=2.6 Hz, 0.5H), 7.43 (d, J=8.4 Hz, 0.5H), 7.45 (d, J=8.4 Hz, 0.5H), 7.60 (dd, J=8.4, 1.5 Hz, 0.5H), 7.66 (dd, J=8.4, 1.5 Hz, 0.5H), 7.95 (d, J=8.4 Hz, 0.5H), 7.96 (d, J=8.8 Hz, 0.5H), 8.17 (br s, 1H). LCMS: m/e 693 (M+H)⁺, ret time 3.24 min, 4 minute gradient.

EXAMPLE 15

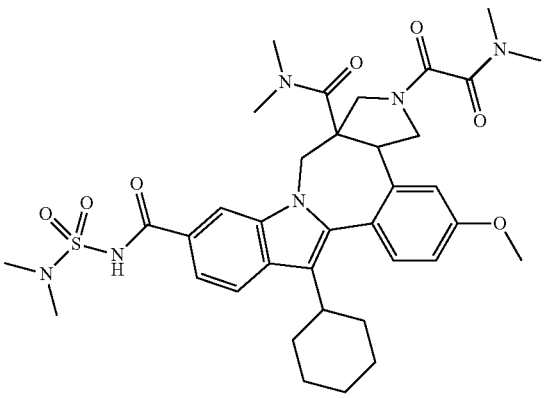

rac-(3aR,14bR)-10-Cyclohexyl-2-((dimethylamino)(oxo)acetyl)-N[7]-(dimethylsulfamoyl)-13-methoxy-N[3a],N[3a]-dimethyl-1,2,3,14b-tetrahydroindolo[2,1-a]pyrrolo[3,4-d][2]benzazepine-3a,7(4H)-dicarboxamide. HATU (37.5 mg, 0.099 mmol) was added to a solution of rac-(3aR,14bR)-10-cyclohexyl-N[7]-(dimethylsulfamoyl)-13-methoxy-N[3a],N[3a]-dimethyl-1,2,3,14b-tetrahydroindolo[2,1-a]pyrrolo[3,4-d][2]benzazepine-3a,7(4H)-dicarboxamide (30 mg, 0.049 mmol) and 2-(dimethylamino)-2-oxoacetic acid (12 mg, 0.10 mmol) in DMF (1 mL) and TEA (0.03 mL, 0.2 mmol). The reaction mixture was stirred at rt for 3 h, diluted with MeOH, and purified by preparative HPLC ($H_2O$/MeOH with 0.1% TFA buffer) to yield rac-(3aR,14bR)-10-cyclohexyl-2-((dimethylamino)(oxo)acetyl)-N[7]-(dimethylsulfamoyl)-13-methoxy-N[3a],N[3a]-dimethyl-1,2,3,14b-tetrahydroindolo[2,1-a]pyrrolo[3,4-d][2]benzazepine-3a,7(4H)-dicarboxamide (15.3 mg, 0.022 mmol, 44% yield) as a white solid. Complex mixture of rotamers was observed, partial $^1$H NMR (aromatic region) reported for 3 major rotamers (5:3:2 ratio). $^1$H NMR (300 MHz, $CD_3OD$) δ 7.05-7.17 (m, 1H), 7.19 (d, J=2.6 Hz, 0.2H), 7.25 (d, J=2.6 Hz, 0.3H), 7.27 (d, J=2.6 Hz, 0.5H), 7.38-7.45 (m, 0.2H), 7.41 (d, J=8.4 Hz, 0.5H), 7.43 (d, J=8.4 Hz, 0.3H), 7.57 (dd, J=8.4, 1.5 Hz, 0.2H), 7.62 (dd, J=8.4, 1.5 Hz, 0.3H), 7.65 (dd, J=8.8, 1.5 Hz, 0.5H), 7.72 (br s, 0.2H), 7.87 (d, J=8.4 Hz, 0.2H), 7.93 (d, J=8.4 Hz, 0.3H), 7.95 (d, J=8.8 Hz, 0.5H), 8.12 (d, J=1.5 Hz, 0.3H), 8.19 (d, J=1.5 Hz, 0.5H). LCMS: m/e 707 (M+H)$^+$, ret time 3.69 min, 4 minute gradient.

EXAMPLE 16

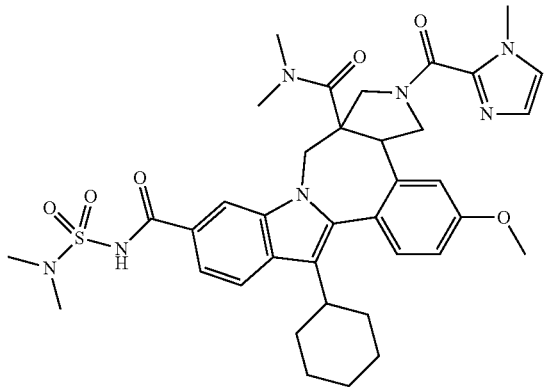

rac-(3aR,14bR)-10-Cyclohexyl-N[7]-(dimethylsulfamoyl)-13-methoxy-N[3a],N[3a]-dimethyl-2-((1-methyl-1H-imidazol-2-yl)carbonyl)-1,2,3,14b-tetrahydroindolo[2,1-a]pyrrolo[3,4-d][2]benzazepine-3a,7(4H)-dicarboxamide. HATU (37.5 mg, 0.099 mmol) was added to a solution of rac-(3aR,14bR)-10-cyclohexyl-N[7]-(dimethylsulfamoyl)-13-methoxy-N[3a],N[3a]-dimethyl-1,2,3,14b-tetrahydroindolo[2,1-a]pyrrolo[3,4-d"][2]benzazepine-3a,7(4H)-dicarboxamide (30 mg, 0.049 mmol) and 1-methyl-1H-imidazole-2-carboxylic acid (12.5 mg, 0.099 mmol) in DMF (1 mL) and TEA (0.03 mL, 0.2 mmol). The reaction mixture was stirred at rt for 16 h, diluted with MeOH, and purified by preparative HPLC ($H_2O$/MeOH with 0.1% TEA buffer) to yield rac-(3aR,14bR)-10-cyclohexyl-N[7]-(dimethylsulfamoyl)-13-methoxy-N[3a],N[3a]-dimethyl-2-((1-methyl-1H-imidazol-2-yl)carbonyl)-1,2,3,14b-tetrahydroindolo[2,1-a]pyrrolo[3,4-d][2]benzazepine-3a,7(4H)-dicarboxamide (20.3 mg, 0.028 mmol, 57% yield) as a bright yellow solid. Complex mixture of rotamers was observed, partial NMR (aromatic region) reported for 2 major rotamers (~3:2 ratio). $^1$H NMR (500 MHz, DMSO-$d_6$) δ 6.78 (s, 0.6H), 6.91 (s, 0.4H), 7.00 (s, 0.4H), 7.05 (s, 0.4H), 7.08-7.22 (m, 2.2H), 7.32 (d, J=8.2 Hz, 0.6H), 7.37 (d, J=8.2 Hz, 0.4H), 7.54 (dd, J=8.6, 1.2 Hz, 0.4H), 7.61 (dd, J=8.6, 1.2 Hz, 0.6H), 7.81 (d, J=8.6 Hz, 0.6H), 7.84 (d, J=8.6 Hz, 0.4H), 8.09 (br s, 0.4H), 8.31 (br s, 0.6H), 11.31 (s, 0.4H), 11.69 (s, 0.6H), LCMS: m/e 716 (M+H)$^+$, ret time 3.67 min, 4 minute gradient.

EXAMPLE 17a and 17b

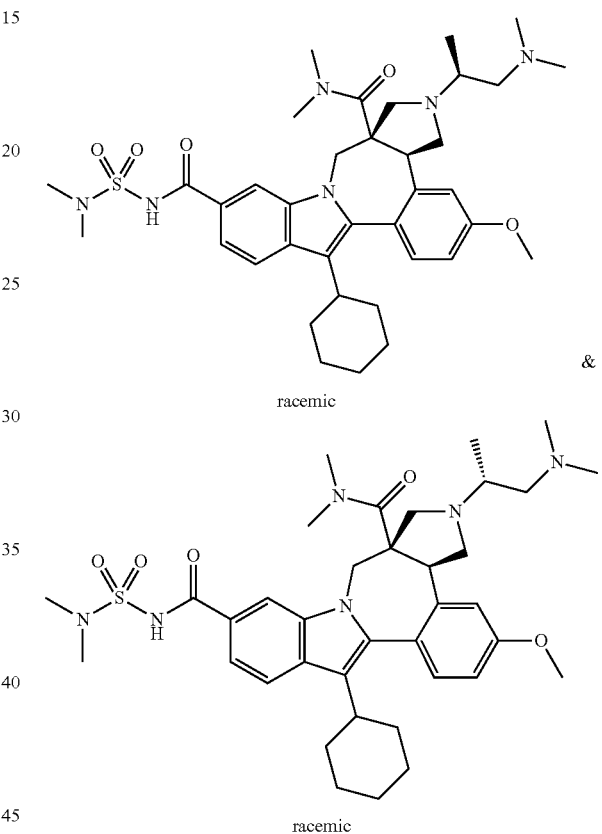

rac-(3aR,14bR)-10-Cyclohexyl-2-(2-(dimethylamino)-1R-methylethyl)-N[7]-(dimethylsulfamoyl)-13-methoxy-N[3a],N[3a]-dimethyl-1,2,3,14b-tetrahydroindolo[2,1-a]pyrrolo[3,4-d][2]benzazepine-3a,7(4H)-dicarboxamide and rac-(3aR,14bR)-10-cyclohexyl-2-(2-(dimethylamino)-1S-methylethyl)-N[7]-(dimethylsulfamoyl)-13-methoxy-N[3a],N[3a]-dimethyl-1,2,3,14b-tetrahydroindolo pyrrolo[3,4-d][2]benzazepine-3a,7(4H)-dicarboxamide. (Dimethylamino)acetone (0.020 mL, 0.18 mmol) and then NaCNBH$_3$ (12.4 mg, 0.20 mmol) were added to a suspension of rac-(3aR,14bR)-10-cyclohexyl-N[7]-(dimethylsulfamoyl)-13-methoxy-N[3a],N[3a]-dimethyl-1,2,3,14b-tetrahydroindolo[2,1-c]pyrrolo[3,4-d][2]benzazepine-3a,7(4H)-dicarboxamide (30 mg, 0.049 mmol) in MeOH (2 mL). The reaction mixture was stirred at rt for 4 h, diluted with DMF (1 mL) and treated with additional (dimethylamino)acetone (0.4 mL). The reaction mixture was stirred at rt for 16 h, diluted with MeOH, and purified by preparative HPLC ($H_2O$/MeOH with 0.1% TFA buffer) to yield the product as a diastereomeric mixture. The material was repurified by preparative HPLC ($H_2O$/$CH_3CN$ with 10 mM NH₄OAc buffer) to yield two sets of isomeric products: Racemate pair A: the product with the shorter retention time on reverse phase HPLC, rac-(3aR,14bR)-10-cyclohexyl-2-(2-(dimethylamino)-1R-methylethyl)-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4H)-dicarboxamide (6.2 mg, 9.0 μmol, 18% yield) as an off-white solid. LCMS: m/e 693 (M+H)⁺, ret time 2.30 min, 4 minute gradient. Column: phenomenex 10u C18 4.6×30 mm; Racemate pair B: the product with the longer retention time on reverse phase HPLC, rac-(3aR,14bR)-10-cyclohexyl-2-(2-(dimethylamino)-1S-methylethyl)-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4H)-dicarboxamide (2.4 mg, 3.5 μmol, 7% yield) as an off-white solid. ¹H NMR (300 MHz, CD₃OD) δ 0.26 (d, J=6.2 Hz, 3H), 1.18-2.25 (m, 12H), 2.34 (d, J=9.9 Hz, 1H), 2.61 (s, 6H), 2.54-2.88 (m, 3H), 2.91 (s, 6H), 2.94-3.38 (m, 7H), 3.91 (s, 3H), 3.98-4.08 (m, 2H), 4.56 (d, J=15.0 Hz, 1H), 4.78-4.94 (m, 1H), 7.06 (dd, J=8.4, 2.6 Hz, 1H), 7.17 (d, J=8.4 Hz, 1H), 7.40 (d, J=8.4 Hz, 1H), 7.77 (d, J=8.4 Hz, 1H), 7.82 (d, J=8.4 Hz, 1H), 8.17 (s, 1H). LCMS: m/e 693 (M+H)⁺, ret time 2.43 min, 4 minute gradient. Column: phenomenex 10u C18 4.6×30 mm.

EXAMPLE 18

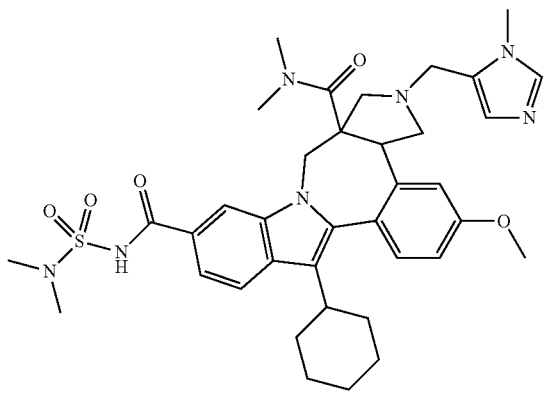

rac-(3aR,14bR)-10-Cyclohexyl-N⁷-(dimethylsulfamoyl)-13-methoxy-N³ᵃ,N³ᵃ-dimethyl-2-((1-methyl-1H-imidazol-5-yl)methyl)-1,2,3,14b-tetrahydroindolo[2,1-a]pyrrolo[3,4-d][2]benzazepine-3a,7(4H)-dicarboxamide. 1-Methyl-1H-imidazole-5-carbaldehyde (16.3 mg, 0.15 mmol) and then NaCNBH₃ (9.3 mg, 0.15 mmol) were added to a slurry of rac-(3aR,14bR)-10-cyclohexyl-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4l7)-dicarboxamide (30 mg, 0.049 mmol) in MeOH (2 mL). The reaction mixture was stirred at rt for 4 h, diluted with THF (1 mL) and treated with additional 1-methyl-1H-imidazole-5-carbaldehyde (25 mg). The reaction mixture was stirred at rt for 16 h, diluted with DMF (1 mL) and treated with additional NaCNBH₃ (10 mg). The reaction mixture was stirred at it for 1d, diluted with MeOH, and purified by preparative HPLC (H₂O/MeOH with 0.1% TFA buffer) to yield rac-(3aR,14bR)-10-cyclohexyl-N⁷-(dimethylsulfamoyl)-13-methoxy-Nᵃ,Nᵃ-dimethyl-2-((1-methyl-1H-imidazol-5-yl)methyl)-1,2,3,14b-tetrahydroindolo[2,1-a]pyrrolo[3,4-d][2]benzazepine-3a,7(4H)-dicarboxamide (20.2 mg, 0.029 mmol, 58% yield) as a white solid. ¹H NMR (300 MHz, CD₃OD) δ 1.25-1.65 (m, 4H), 1.77-2.23 (m, 7H), 2.66 (d, J=10.6 Hz, 1H), 2.94-3.07 (m, 2H), 3.05 (s, 6H), 3.10-3.35 (m, 6H), 3.51 (d, J=15.0 Hz, 1H), 3.58 (d, J=15.0 Hz, 1H), 3.64 (s, 3H), 3.79 (d, J=10.6 Hz, 1H), 3.91 (s, 3H), 4.04 (d, J=15.0 Hz, 1H), 4.15 (dd, J=10.6, 7.7 Hz, 1H), 4.52 (d, J=15.0 Hz, 1H), 7.06-7.15 (m, 3H), 7.41 (d, J=8.4 Hz, 1H), 7.65 (dd, J=8.4, 1.5 Hz, 1H), 7.95 (d, J=8.4 Hz, 1H), 8.03 (d, J=1.5 Hz, 1H), 8.55 (br s, 1H). LCMS: m/e 702 (M+H)⁴, ret time 3.16 min, 4 minute gradient.

EXAMPLE 19

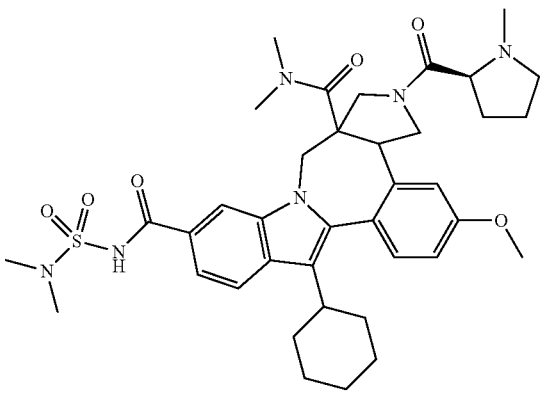

rac-(3aR,14bR)-10-Cyclohexyl-N⁷-(dimethylsulfamoyl)-13-methoxy-N³ᵃ,N³ᵃ-dimethyl-2-(1-methyl-L-prolyl)-1,2,3,14b-tetrahydroindolo[2,1-a]pyrrolo[3,4-d]benzazepine-3a,7(4H)-dicarboxamide. HATU (37.5 mg, 0.099 mmol) was added to a solution of rac-(3aR,14bR)-10-cyclohexyl-N⁷-(dimethylsulfamoyl)-13-methoxy-N³ᵃ,N³ᵃ-dimethyl-1,2,3,14b-tetrahydroindolo[2,1-a]pyrrolo[3,4-d][2]benzazepine-3a,7(4H)-dicarboxamide (30 mg, 0.049 mmol) and (S)-1-methylpyrrolidine-2-carboxylic acid hydrochloride (12.3 mg, 0.074 mmol) in DMF (1 mL) and TEA (0.03 mL, 0.2 mmol). The reaction mixture was stirred at rt for 3 h, diluted with MeOH, and purified by preparative HPLC (H₂O/MeOH with 0.1% TFA buffer) to yield rac-(3aR,14bR)-10-cyclohexyl-N⁷-(dimethylsulfamoyl)-13-methoxy-N³ᵃ,N³ᵃ-dimethyl-2-(1-methyl-L-prolyl)-1,2,3,14b-tetrahydroindolo[2,1-a]pyrrolo[3,4-d][2]benzazepine-3a,7(4H)-dicarboxamide (24.3 mg, 0.034 mmol, 69% yield) as a white solid. Complex mixture of diastereomers. ¹H NMR (300 MHz, CD₃OD) δ 1.21-2.26 (m, 14H), 2.51-3.07 (m, 11H), 3.10-3.30 (m, 6H), 3.43-3.86 (m, 3H), 3.94 (s, 3H), 3.91-4.65 (m, 5H), 4.72-4.96 (m, 1H), 7.07-7.15 (m, 1H), 7.26-7.33 (m, 1H), 7.40-7.50 (m, 1H), 7.53-7.72 (m, 1H), 7.87-7.99 (m, 1H), 8.16-8.21 (m, 1H). LCMS: in/e 719 (M+H)⁴, ret time 3.21 min, 4 minute gradient.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

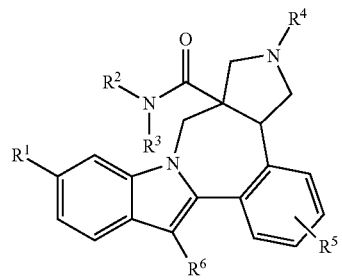

$R^1$ is $CO_2R^7$ or $CONR^8R^9$;
$R^2$ is hydrogen or alkyl;
$R^3$ is hydrogen or alkyl;
or $NR^2R^3$ taken together is azetidinyl, pyrrolidinyl, piperidinyl, piperazinyl, N-(alkyl)piperazinyl, morpholinyl, thiomorpholinyl, homopiperidinyl, or homomorpholinyl, and is substituted with 0-3 alkyl substituents;
or $NR^2R^3$ taken together is

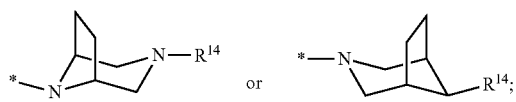

$R^4$ is hydrogen, alkyl, alkylCO, $(R^{13})$alkyl, $((R^{13})$alkyl)CO, $(R^{13})$CO, $(R^{13})$COCO, $(Ar^1)$alkyl, $(Ar^1)$CO, or $(Ar^1)$COCO;
$R^5$ is hydrogen, halo, alkyl, alkenyl, hydroxy, benzyloxy, or alkoxy;
$R^6$ is cycloalkyl;
$R^7$ is hydrogen or alkyl;
$R^8$ is hydrogen, alkyl, alkylSO$_2$, cycloalkylSO$_2$, haloalkylSO$_2$,$(R^{10})(R^{11})$NSO$_2$, or$(R^{12})$SO$_2$;
$R^9$ is hydrogen or alkyl;
$R^{10}$ is hydrogen or alkyl;
$R^{11}$ is hydrogen or alkyl;
$R^{12}$ is azetidinyl, pyrrolidinyl, piperidinyl, piperazinyl, N-(alkyl)piperazinyl, morpholinyl, thiomorpholinyl, homopiperidinyl, or homomorpholinyl;
$R^{13}$ is amino, alkylamino, or dialkylamino,
or $R^{13}$ is azetidinyl, pyrrolidinyl, piperidinyl, piperazinyl, N-(alkyl)piperazinyl, morpholinyl, thiomorpholinyl, homopiperidinyl, or homomorpholinyl, and is substituted with 0-3 alkyl substituents;
$R^{14}$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl; and
$Ar^1$ is phenyl, pyrrolyl, pyrazolyl, imidazolyl, or triazolyl, and is substituted with 0-2 alkyl substituents;
or a pharmaceutically acceptable salt thereof.

2. A compound of claim 1 where $R^1$ is $CONR^8R^9$; $R^2$ is alkyl; $R^3$ is alkyl; or $NR^2R^3$ taken together is morpholinyl substituted with 2 alkyl substituents; $R^4$ is hydrogen, alkyl, alkylCO, $(R^{13})$alkyl, $((R^{13})$alkyl)CO, $(R^{13})$CO, $(R^{13})$COCO, $(Ar^1)$alkyl, or $(Ar^1)$CO; $R^5$ is alkoxy; $R^6$ is cycloalkyl; $R^8$ is $(R^{10})(R^{11})$NSO$_2$; $R^9$ is hydrogen; $R^{10}$ is alkyl; $R^{11}$ is alkyl; $R^{13}$ is dialkylamino, or $R^{13}$ is pyrrolidinyl and is substituted with 0-3 alkyl substituents; and $Ar^1$ is phenyl, or imidazolyl, and is substituted with 0-2 alkyl substituents; or a pharmaceutically acceptable salt thereof.

3. A compound of claim 2 where $R^1$ is CONHSO$_2$NMe$_2$; $R^2$ is methyl; $R^3$ is methyl; or $NR^2R^3$ taken together is morpholinyl substituted with 2 methyl substituents; $R^4$ is hydrogen, methyl, isopropyl, benzyl, acetyl, CONMe$_2$, N,N-dimethylaminopropyl, COCH$_2$NMe$_2$, COCONMe$_2$, (methylimidazolyl)methyl, (methylimidazolyl)CO, or (methylpyrrolidinyl)CO; $R^5$ is methoxy; $R^6$ is cyclohexyl; or a pharmaceutically acceptable salt thereof.

4. A compound of claim 1 where $R^1$ is $CONR^8R^9$; $R^8$ is alkylSO$_2$, cycloalkylSO$_2$, haloalkylSO$_2$, $(R^{10})(R^{11})$NSO$_2$, or $(R^{12})$SO$_2$; and $R^9$ is hydrogen.

5. A compound of claim 1 where $R^5$ is hydrogen.

6. A compound of claim 1 where $R^5$ is methoxy.

7. A compound of claim 1 where $R^6$ is cyclohexyl.

8. A compound of claim 1 where $R^8$ is$(R^{10})(R^{11})$NSO$_2$ or $(R^{12})$SO$_2$.

9. A compound of claim 1 with the following stereochemistry

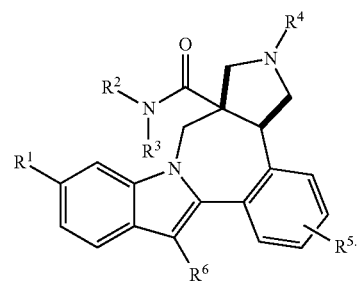

10. A compound of claim 1 selected from the group consisting of

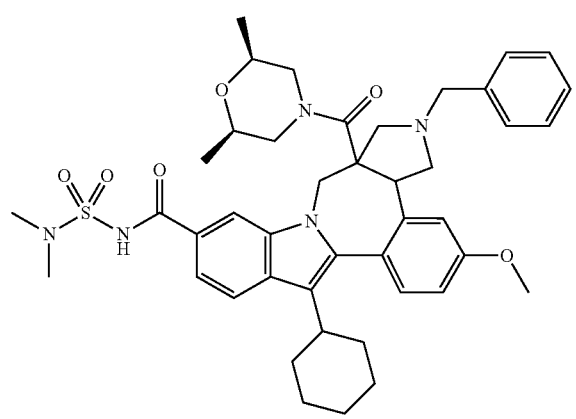

45
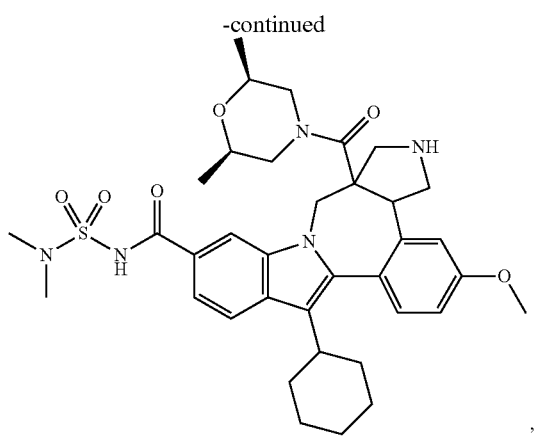
46
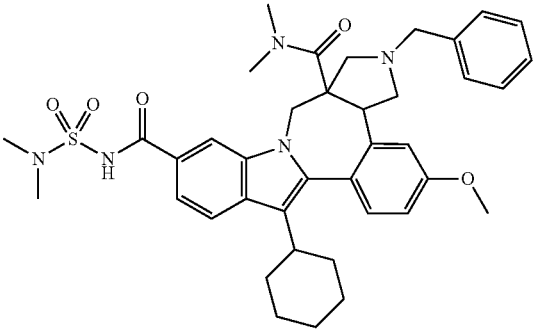
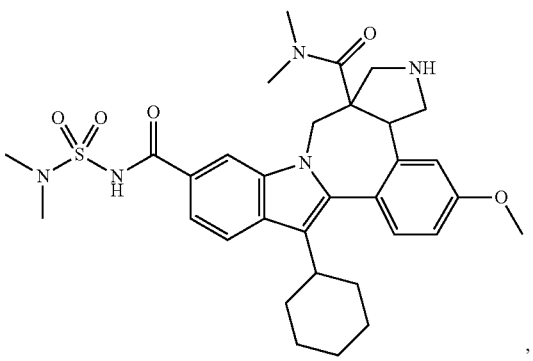
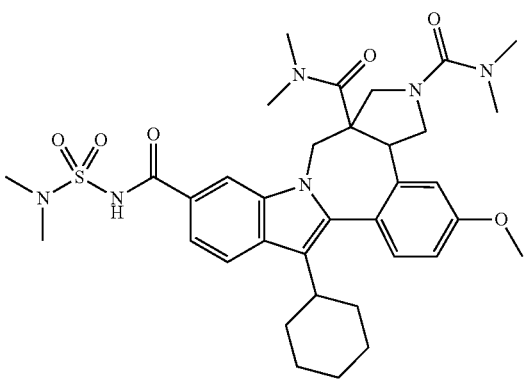
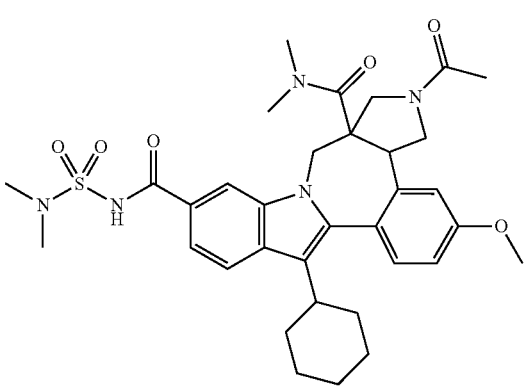

47
-continued
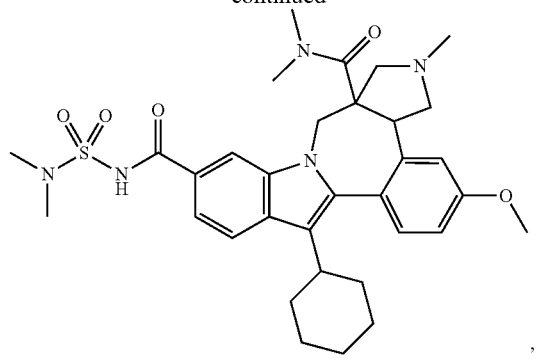
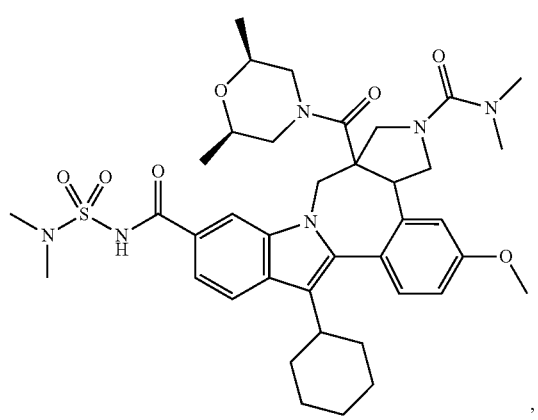
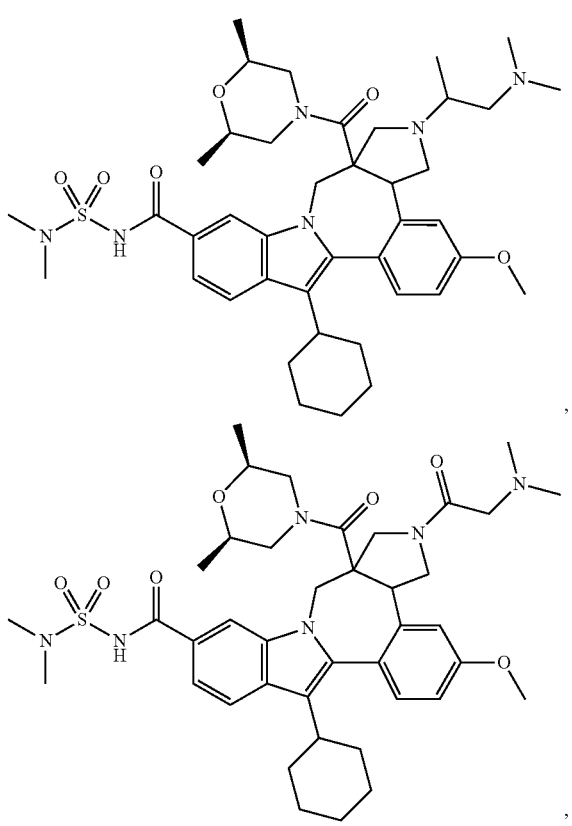
48
-continued
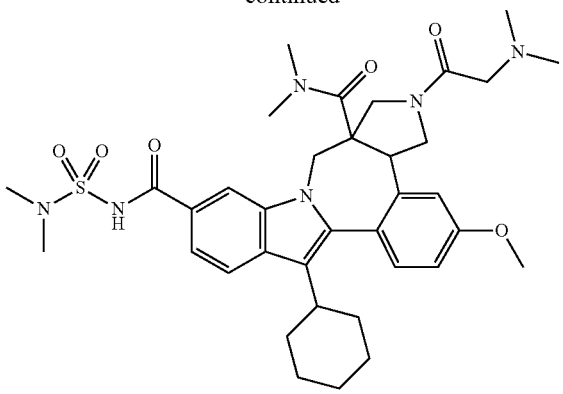
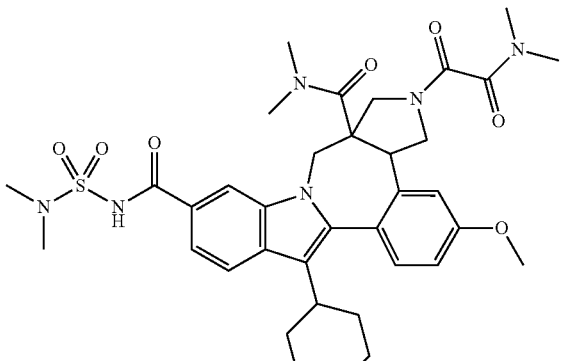
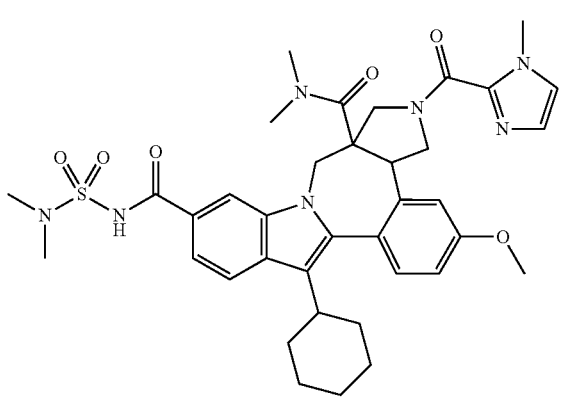
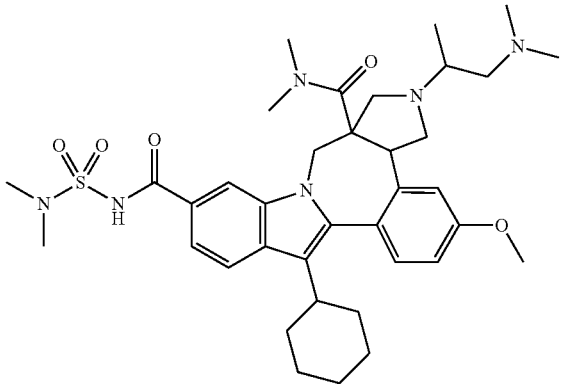

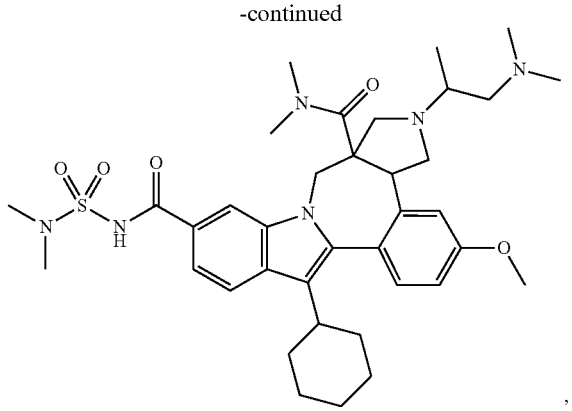
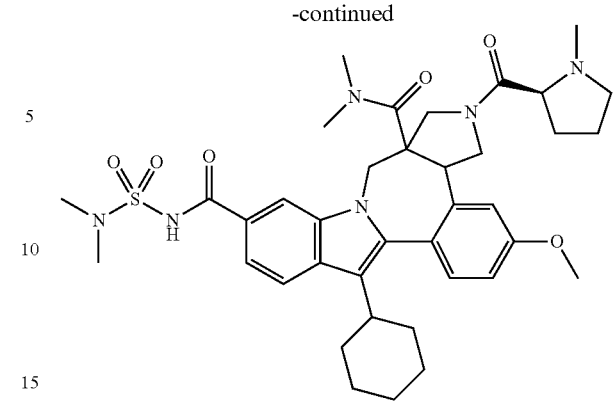
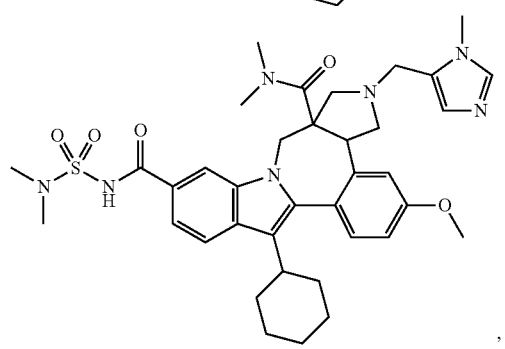
, and
or a pharmaceutically acceptable salt thereof.
11. A composition comprising a compound of claim 1, or a pharmaceutically acceptable salt thereof, and a pharmaceutically acceptable carrier.
12. A method of treating hepatitis C infection comprising administering a therapeutically effective amount of a compound of claim 1 to a patient.
\* \* \* \* \*

UNITED STATES PATENT AND TRADEMARK OFFICE
CERTIFICATE OF CORRECTION

PATENT NO.        : 8,119,628 B2                                               Page 1 of 1
APPLICATION NO.   : 12/922752
DATED             : February 21, 2012
INVENTOR(S)       : Zhong Yang et al.

It is certified that error appears in the above-identified patent and that said Letters Patent is hereby corrected as shown below:

In the Claims:

Claim 1:

Column 43, lines 28 to 31, change

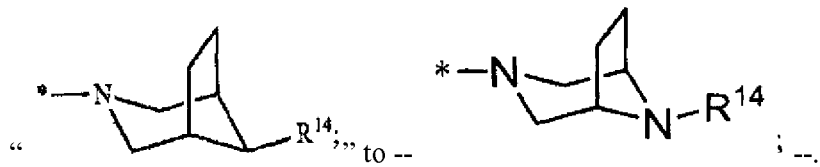

Column 43, line 43, change "haloalkylSO$_2$,(R$^{10}$)(R$^{11}$)NSO$_2$, or(R$^{12}$)SO$_2$;" to -- haloalkylSO$_2$, (R$^{10}$)(R$^{11}$)NSO$_2$, or (R$^{12}$)SO$_2$; --.

Claim 8:

Column 44, line 26, change "is(R$^{10}$)(R$^{11}$)NSO$_2$" to -- is (R$^{10}$)(R$^{11}$)NSO$_2$ --.

Signed and Sealed this
First Day of July, 2014

Michelle K. Lee
*Deputy Director of the United States Patent and Trademark Office*